United States Patent
Aguilera

(10) Patent No.: US 12,201,626 B2
(45) Date of Patent: Jan. 21, 2025

(54) BIFUNCTIONAL COMPOSITIONS FOR THE TREATMENT OF CANCER

(71) Applicant: ARMACEUTICA, INC., El Paso, TX (US)

(72) Inventor: Renato Aguilera, El Paso, TX (US)

(73) Assignee: Armaceutica, Inc., El Paso, TX (US)

( * ) Notice: Subject to any disclaimer, the term of this patent is extended or adjusted under 35 U.S.C. 154(b) by 0 days.

(21) Appl. No.: 17/041,800

(22) PCT Filed: Jun. 19, 2019

(86) PCT No.: PCT/IB2019/055130
§ 371 (c)(1),
(2) Date: Sep. 25, 2020

(87) PCT Pub. No.: WO2019/244050
PCT Pub. Date: Dec. 26, 2019

(65) Prior Publication Data
US 2021/0361643 A1 Nov. 25, 2021

(30) Foreign Application Priority Data
Jun. 19, 2018 (AU) ................. 2018902181

(51) Int. Cl.
| | | |
|---|---|---|
| *A61K 31/4745* | (2006.01) | |
| *A61K 31/337* | (2006.01) | |
| *A61K 31/404* | (2006.01) | |
| *A61K 31/4184* | (2006.01) | |
| *A61K 31/454* | (2006.01) | |
| *A61K 31/506* | (2006.01) | |
| *A61K 31/519* | (2006.01) | |
| *A61K 31/69* | (2006.01) | |
| *A61K 31/704* | (2006.01) | |
| *A61K 31/7068* | (2006.01) | |
| *A61K 33/243* | (2019.01) | |
| *A61K 38/06* | (2006.01) | |
| *A61K 38/50* | (2006.01) | |
| *A61P 35/00* | (2006.01) | |

(52) U.S. Cl.
CPC ........ *A61K 31/4745* (2013.01); *A61K 31/337* (2013.01); *A61K 31/404* (2013.01); *A61K 31/4184* (2013.01); *A61K 31/454* (2013.01); *A61K 31/506* (2013.01); *A61K 31/519* (2013.01); *A61K 31/69* (2013.01); *A61K 31/704* (2013.01); *A61K 31/7068* (2013.01); *A61K 33/243* (2019.01); *A61K 38/06* (2013.01); *A61K 38/50* (2013.01); *A61P 35/00* (2018.01)

(58) Field of Classification Search
CPC ................. A61K 31/4745; A61P 35/00
See application file for complete search history.

(56) References Cited

U.S. PATENT DOCUMENTS

| 2011/0300137 A1 | 12/2011 | Mckenzie |
| 2012/0172292 A1 | 7/2012 | Nudler et al. |

FOREIGN PATENT DOCUMENTS

| CN | 1280826 A | * | 1/2001 |
| WO | 2018/235103 | | 12/2018 |

OTHER PUBLICATIONS

English Machine Translation of CN1280826A (Published Jan. 24, 2001) (9 pages) (Year: 2001).*
Qi et al. Biochemical and Biophysical Research Communications, 2004, vol. 319, pp. 1124-1131 (Year: 2004).*
Asadi-Pooya et al. Medical Hypothesis, 2007, vol. 69, pp. 560-563 (Year: 2007).*
International Search Report for PCT/IB2019/005130 mailed Aug. 7, 2019, 5 pgs.
Zhu, H., et al. "Nanodiamond mediated co-delivery of doxorubicin and malaridine to maximize synergistic anti-tumor effects on multi-drug resistant MCF-7/ADR cells," Journal of Materials Chemistry B, 2017, p. 3531-3540.
Qi, J., et al., "Functiona nd mechanism of pyronaridine: a new inhibitor of P-glycoprotein-mediated multidrug resistance," Aeta Pharmacologica Sinica, 2002, p. 514-550, vol. 23, No. 6.
Li, D., et al, "Synthesis and biological research of novel azaacridine derivatives as potent DNA-binding ligands and topoisomerase II inhibitors," Bioorganic & Medicinal Chemistry, 2017, p. 3437-3446, vol. 25.
Luan, X., et al., "Novel Synthetic Azaacridine Analogues as Topoisomerase 1 Inhibitors," Chemistry Letters 2011, p. 728-729, vol. 40.
Otta, D.A., et al., "Identification of Anti-Trypanosoma cruzi Lead Compounds with Putative Immunomodulatory Activity," 2018, p. 1-13, vol. 62, No. 4.
Wang, Y. et al., "pH redox and photothermal tri-responsive DNA/ polyethylenimine conjugated gold nanorods as nanocarriers for specific intracellular co-release of doxorubicin and chemosensitizer pyronaridine to combat multidrug resistant cancer," Nanomedicine: Nanotechnology, Biology, and Medicine, 2017, p. 1785-1795, vol. 13.
Marylin Madamet et al., The Plasmodium Falciparum Chloroquine Resistance Transporter is Associated with the Ex Vivo P. Falciparum African Parasite Response to Pyronnaridine, Parassies & Vectors, 2016, 9:77, 5 pages.

(Continued)

*Primary Examiner* — James D. Anderson
(74) *Attorney, Agent, or Firm* — LOWENSTEIN SANDLER LLP

(57) ABSTRACT

The present invention relates to the use of bifunctional compositions in methods of treating or preventing cancer. The compositions comprise a DNA ligand and a protein ligand for the treatment or prevention of cancer, wherein the DNA ligand interferes with DNA metabolism and the protein ligand interferes with signaling pathways. In particular, the present invention relates to the use of pyronaridine in methods of treating of preventing cancer. The invention also relates to compositions, compounds and medicaments comprising a DNA ligand and a protein ligand, for example, compositions, compounds and medicaments comprising pyronaridine.

9 Claims, 10 Drawing Sheets

(56) References Cited

OTHER PUBLICATIONS

Aura Rank et al., "Multiple Approaches to Repurposing Drugs for Neuroblastoma", Bioorganic & Medicinal Chemistry, 2022, vol. 73, 8 pages.
Jeevan Ghosalkar et al., "Prostate Apoptosis Response-4 (Par-4): A Novel Target in Pyronaridine-Induced Apoptosis in Glioblastoma (GBM) Cells", Cancers, 2022, vol. 14, 25 pages.
Office Action issued by United States Patent Office for U.S. Appl. No. 13/134,212 mailed on May 26, 2015, 22 pages.
Office Action issued by United States Patent Office for U.S. Appl. No. 13/134,212 mailed on Jun. 6, 2013. 17 pages.

* cited by examiner

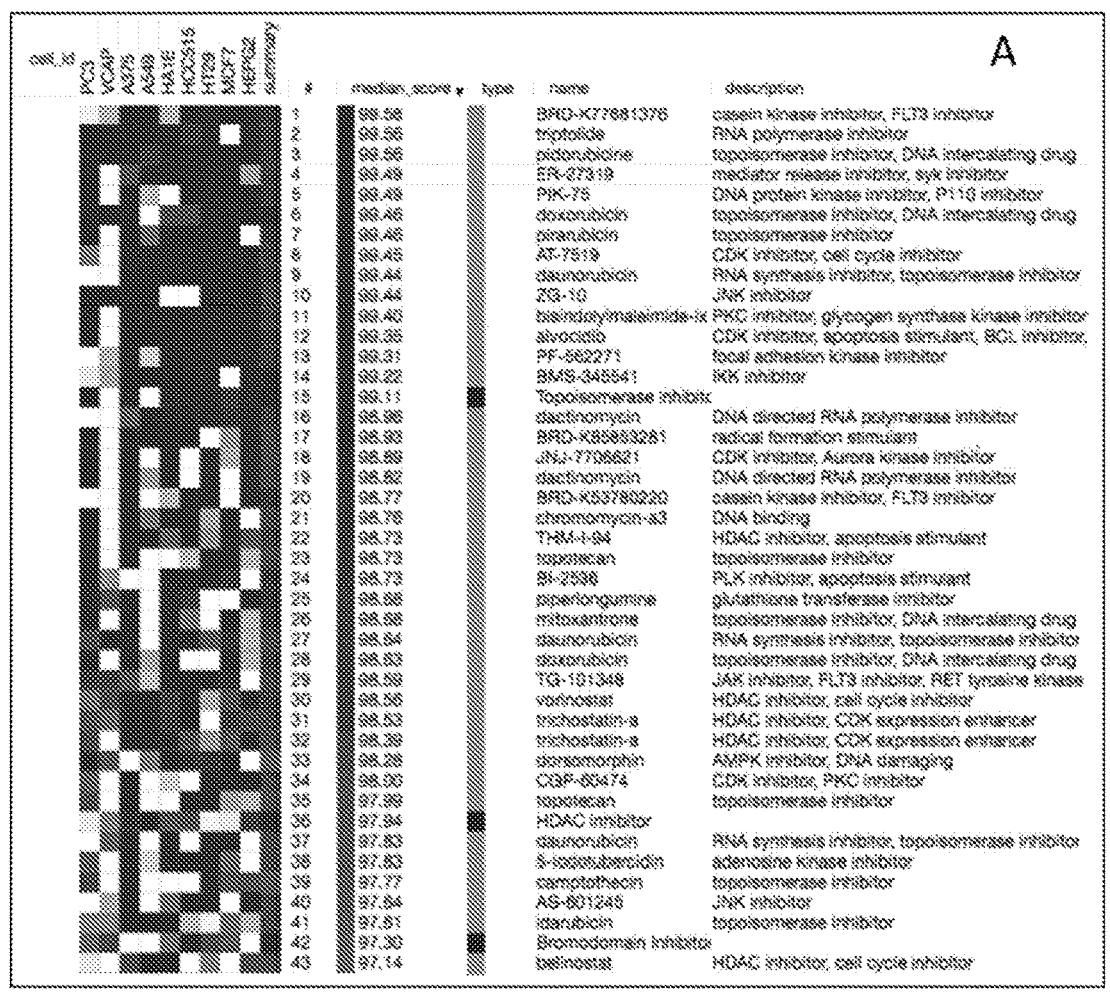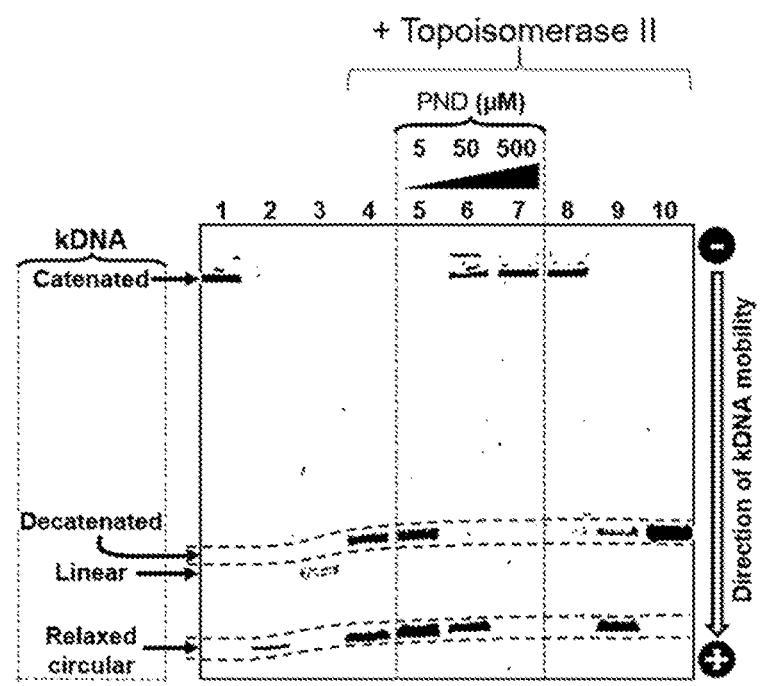
Figure 3

| Cell Type | Cell Line Name | $CC_{50}$ µM | SCI |
|---|---|---|---|
| Breast Cancer | MDA-MB-231 | 1.6 ± 0.20[†] | 4.1 |
| Breast Cancer | MDA-MB-231 LM2[‡] | 2.6 ± 0.18 | 2.5 |
| Breast Cancer | MDA-MB-468 | 1.7 ± 0.60 | 3.9 |
| Breast Cancer | T47D | 9.4 ± 1.41 | 0.7 |
| Breast Cancer | HCC1419 | 7.0 ± 0.33 | 0.9 |
| Breast Cancer | MCF-7 | 1.6 ± 0.40 | 4.1 |
| Breast Cancer | HCC-70 | 1.5 ± 0.51 | 4.4 |
| Breast Epethelial | MCF-10A | 6.6 ± 0.42 | 1.0 |
| Normal Fibroblast | HS-27 | 3.1 ± 0.39 | 2.1 |
| Leukemia | HL-60 | 1.9 ± 0.07 | 3.5 |
| Burkitt's Lymphoma | Ramos | 2.2 ± 0.16 | 3.0 |
| T-cell Lymphoma | Jurkat | 2.0 ± 0.11 | 3.3 |
| T-cell Lymphoma | CEM | 4.6 ± 0.09 | 1.4 |
| Melanoma | A375 | 2.0 ± 0.03 | 3.2 |
| Ovarian Cancer | Ovcar 8 | 1.7 ± 0.22 | 3.9 |
| Ovarian Cancer | Ovcar 5 | 1.7 ± 0.06 | 3.9 |
| Ovarian Cancer | Ovcar 3 | 3.3 ± 0.02 | 2.0 |
| Lung Cancer | A549 | 3.5 ± 0.21 | 1.9 |
| Pancreatic Cancer | Panc-1 | 6.5 ± 0.07 | 1.0 |

[†] Mean ± Standard Deviation
[‡] Lung Metastatic (LM) variant of MDA-MB-231

Figure 5

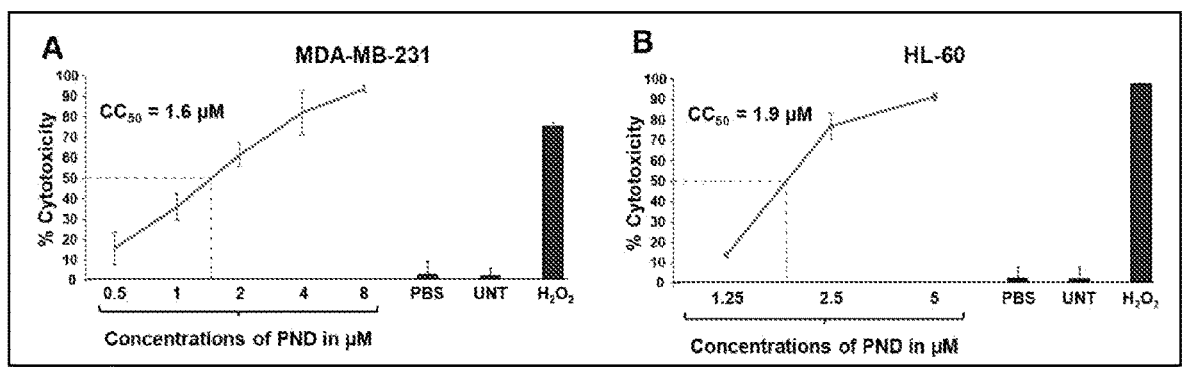

Figure 6

BIFUNCTIONAL COMPOSITIONS FOR THE TREATMENT OF CANCER

FIELD OF THE INVENTION

The present invention relates to methods of treating or preventing cancer. In particular, the invention contemplates the use of bifunctional compositions and compounds in the treatment or prevention of cancer. The invention more specifically relates to the use of compositions comprising a DNA ligand and a protein ligand for the treatment or prevention of cancer. The invention also relates to compositions, compounds and medicaments comprising a DNA intercalator and a protein inhibitor.

BACKGROUND OF THE INVENTION

Any discussion of the prior art throughout the specification should in no way be considered as an admission that such prior art is widely known or forms part of common general knowledge in the field.

Survival rates from cancers are often very closely linked to the frequency of early diagnosis, the aggressiveness of the cancer, the availability of effective anti-cancer therapies that are targeted to the cancer, the overall health of the subject undergoing treatment, and/or whether there are options, surgical or otherwise, for the removal of tumours and cancerous cells.

All types of cancer are generally characterized by uncontrolled cell division through aberrant molecular signalling that allows cells to circumvent cell-cycle arrest/apoptosis. The persistence of the cellular proliferation is often attributed to, at least in part, the disabling of cellular mechanisms for programmed cell death.

However, common to many cancers is the fact that indiscriminate therapeutic agent targeting, and the toxicity of the agents, limits the efficacy of anti-cancer therapies in their treatment.

To circumvent the targeting issue, while also producing therapies that have broad applicability, it can be useful to target cellular processes that are significantly increased in the cell proliferation associated with cancer, such as DNA transcription and replication required during cell division. The mode of action of such therapies is often related to the subsequent DNA damage initiating apoptotic pathways that lead to cell death. Selective apoptosis of proliferating cancer cells is crucial to effectively treating cancer.

Molecules that bind DNA can interfere with DNA synthesis by blocking interactions between the DNA and, for example, transcription factors, polymerases, ligases, nucleases, topoisomerases and helicases. In particular, DNA ligands that intercalate between the base pairs of DNA strands are especially effective at perturbing the cellular machinery and complexes that associate with, and move along the length of, the DNA during transcription and replication. However, while such DNA ligands may target cancerous cells, they can also impact upon cells undergoing normal cell division, and affect expression in non-dividing cells, leading to a broad range of potential side-effects.

Moreover, the action of a DNA ligand may not be sufficient because, despite the potential therapeutic effect of interfering with DNA synthesis to trigger apoptosis, the ability of cancerous cells to evade cell death may negate the therapeutic benefit associated with inflicting DNA damage to cancerous cells.

As such, it would be advantageous to combine the activity of a DNA ligand with a means of hindering signalling cascades that enhance tumour progression and evasion of cell death and the immune response that may ordinarily be triggered by, for example, a DNA damage response.

One class of molecules involved in evasion of cell death and tumour promotion are the protein kinases, many of which are prolific and promiscuous kinases with vast arrays of substrates. Unfortunately, the inhibition of a protein kinase involved in multiple pathways can often have severe side-effects, which can be a barrier to successful drug development and commercialization.

One strategy to expedite the drug development pathway for new therapies is to repurpose (or reposition) existing licensed drugs for new medical indications. Repurposing is effectively the reuse of drugs with specific indications for new applications, while taking advantage of existing knowledge and safety data. Recent examples of promising repurposing of drugs for the treatment and prevention of cancer include the use of anti-parasitic and anti-psychotic drugs. There have also been in vitro studies of some anti-malarial drugs that were shown to be effective against resistant strains of malaria being repurposed to be co-administered with chemotherapeutic drugs to enhance treatment by countering or reversing resistance to chemotherapeutic drugs. Of course, while repurposing may allow expedition of some aspects of drug development as far as safety data is concerned, it does not circumvent the need to demonstrate the repurposed drug is actually effective for the new application via in vivo studies and human trials, as in vitro data is often not representative of in vivo results.

For example, in US20110300137 there is described the use of the anti-malarial drug, lumefantrine, in conjunction with chemotherapeutic drugs, wherein the lumefantrine enhances the treatment of cancer by inhibiting autophagy. Autophagy is a known mechanism employed by cancer stem cells against chemotherapeutic drugs, that allows the cells to remain in a quiescent state, before proliferating again once the chemotherapeutic drug is removed. In this quiescent state, the cancer cells are protected from the chemotherapeutic drugs, which generally target proliferating cells, thereby contributing the cancer's resistance to the chemotherapeutic drug. By inhibiting autophagy, the cancer cells cannot evade the chemotherapeutic drugs and the resistance is diminished, but it is still the activity of the chemotherapeutic drugs that treats the cancer. However, while the lumefantrine was shown to have anti-autophagy activity in in vitro studies in US20110300137, neither lumefantrine nor any of the multitude of recited anti-malarial drugs (some of which, such as pyronaridine, share very little structural similarity with the other members of the group purported to have the same activity) were shown or suggested to have any anti-proliferative or apoptotic activity to effectively treat or prevent the dividing cells of a cancer alone, nor where there any in vivo studies to validate the findings.

In another example, CN1135977C describes the use of another anti-malarial drug, pyronaridine, in the preparation of combination antineoplastic drugs for the treatment of multidrug resistant tumours. Similarly, this disclosure relates to the co-, or pre-administration of pyronaridine with Adriamycin (ADR: doxorubicin) to multi-drug resistance cell lines with specific resistance to ADR, to enhance the cytotoxic effects of the ADR. While it was shown that apoptosis of the MDR cell lines by ADR could be enhanced in the presence of pyronaridine in in vitro studies, it was not demonstrated or suggested that PND could induce apoptosis in proliferating cells alone, nor that any proposed activity of pyronaridine was transferable and replicable in actual tumours. Accordingly, the invention claimed in CN1135977C is merely for the use of pyronaridine in combination with anti-tumour drugs for the reversal of MDR in resistant tumours in vitro.

It would be useful to be able to repurpose a known drug that has both DNA and protein binding activities, such as an antimalarial drug with a long history of tolerated use, for novel therapeutic applications to expedite the drug development pathway for cancer treatments.

It is an object of the present invention to overcome or ameliorate at least one of the disadvantages of the prior art, or to provide a useful alternative.

SUMMARY OF THE INVENTION

Surprisingly it has been found that a molecule comprising a DNA ligand and a protein ligand is useful for the treatment and prevention of cancer. In particular, the present inventors have found that an antimalarial drug comprising a DNA ligand and a protein ligand, pyronaridine, has previously unknown anti-proliferative activities towards actively dividing cancer cells, wherein the activity is selective, thereby minimizing side-effects. The present inventors are the first to demonstrate in in vivo studies that pyronaridine has selective cytotoxicity and can be used for the treatment and/or prevention of cancer, as opposed to merely enhancing the effect of chemotherapeutic drugs on MDR immortalized cancer cell lines.

Accordingly, in a first aspect of the present invention, there is provided a method of inducing apoptosis in proliferating cancer cells for the treatment or prevention of cancer in a mammal, the method comprising the step of administering to said mammal a composition comprising a therapeutically effective amount of pyronaridine (PND), or a derivative or pharmaceutically acceptable salt thereof.

In a second aspect of the present invention, there is provided a method of inducing apoptosis in proliferating cancer cells in a tumour in a mammal, the method comprising the step of administering to said mammal a composition comprising a therapeutically effective amount of pyronaridine (PND), or a derivative or pharmaceutically acceptable salt thereof.

In a third aspect of the present invention, there is provided a method of inducing cell death in cancer cells in a tumour in a mammal, the method comprising the step of administering to said mammal a composition comprising a therapeutically effective amount of pyronaridine (PND), or a derivative or pharmaceutically acceptable salt thereof.

In a fourth aspect of the present invention, there is provided a method of inducing cell death in cancer cells for the treatment or prevention of cancer in a mammal, the method comprising the step of administering to said mammal a composition comprising a therapeutically effective amount of pyronaridine (PND), or a derivative or pharmaceutically acceptable salt thereof.

In a fifth aspect of the present invention, there is provided a method of reducing the size of a tumour in a mammal, the method comprising the step of administering to said mammal a composition comprising a therapeutically effective amount of pyronaridine (PND), or a derivative or pharmaceutically acceptable salt thereof, wherein the administration reduces the tumour size by inducing apoptosis in proliferating cancer cells in the tumour.

In a sixth aspect of the invention, there is provided a method of treating or preventing cancer, the method comprising the step of administering to a subject in need thereof a composition comprising a DNA ligand and a protein ligand.

The DNA ligand may be any molecule that can bind DNA and interfere with DNA metabolism. By DNA metabolism is meant any cellular process by which DNA is maintained or in which DNA is used and it includes, for example, DNA synthesis and degradation reactions involved in DNA replication and repair, as well as transcription. By replication is meant any process whereby DNA sequences are copied. The ligand may bind the DNA non-specifically through electrostatic interactions, through specific groove-binding interactions, and/or through intercalation between base-pairs. In preferred embodiments, the DNA ligand is a DNA intercalator. The DNA intercalator may act by intercalation of base pairs through the DNA major groove or DNA minor groove, and/or intercalation by threading.

The DNA ligand may comprise a planar ring system that facilitates DNA intercalation by allowing insertion between two adjacent base pairs in the DNA double strands, thereby distorting the DNA double-helix and/or hindering DNA replication and/or transcription by interfering with DNA unwinding, elongation and/or ligation. The interference with DNA synthesis in proliferating cells, such as cancerous cells, can slow or stop DNA replication and cellular proliferation, interfere with the cell-cycle, reduce cell viability and/or lead to cell death.

In particular instances, DNA intercalators can initiate apoptotic pathways by inhibiting topoisomerase activity. These DNA intercalators may be classified as topoisomerase inhibitors or topoisomerase poisons, and may target topoisomerase I and/or topoisomerase II. These DNA intercalators may also bind the topoisomerase proteins. Preferably, the DNA intercalator is capable of also binding and inhibiting the activity of topoisomerase II. Without wishing to be bound by theory, it is proposed that by forming a complex with DNA and topoisomerase II in a proliferating cell undergoing DNA synthesis, the DNA and topoisomerase II becomes trapped in the "cleavable complex". This prevents the re-ligation of the double-stranded DNA which was initially cut by the topoisomerase to facilitate unwinding. The subsequent endogenous DNA strand breaks trigger the DNA damage response, leading to apoptosis. This mode of action may be facilitated, or contributed to, by the DNA intercalator stabilising the double-strand break, and/or preventing re-annealing of the two DNA strands.

In instances where the DNA ligand is an DNA intercalator, the protein ligand of the composition of the invention may also contribute to the initiation of the apoptotic pathway by interacting with the DNA and/or the topoisomerase.

The planar ring system of the DNA intercalator may comprise two or more fused rings. Preferably the rings are aromatic. The rings may be any 5- or 6-membered aromatic compounds and they may be substituted and/or heterocyclic. A substituted aromatic ring is one wherein a hydrogen atom on the ring is substituted by another atom or group. A heterocyclic aromatic compound is one wherein the ring structure comprises carbon and at least one other atom, such as, for example, nitrogen, oxygen and/or sulfur. For example, the DNA intercalator may comprise a benzene ring and/or a 6-membered heterocyclic compound such as pyridine, pyrimidine, pyrazine, phosphinine, diazine and/or thiazine. In other examples, the DNA intercalator may comprise a 5-membered heterocyclic compound such as pyrrole, imidazole, furan, thiazole and/or thiofene.

In preferred embodiments, the planar ring system comprises at least one pyridine ring, though the ring system may comprise 2 or more pyridine rings. The planar ring system may comprise three fused aromatic rings. The three fused rings may be 5- or 6-membered rings. In one embodiment, the planar ring system comprises three fused 6-membered aromatic rings, wherein at least one, and preferably two, of the aromatic rings are heterocyclic. Each of the rings may be benzene, in which case the planar ring system may be referred to as anthracene. One or more of the benzene rings may be halogenated, nitrated, sulfonated, alkylated, acylated and/or substituted with sterically permissible combinations thereof. The DNA intercalator may be a heterocyclic derivative of anthracene, wherein at least one of the rings has a ring structure comprising carbon and at least nitrogen. Derivatives of anthracene with a ring structure comprising carbon and one, two and three nitrogens may be referred to as monazaanthracenes, diazaanthracene and triazaanthracene, respectively.

Non-limiting examples of anthracenes/anthracene groups that may form part of the DNA intercalator include 1,-monoazaanthracene, 2,-monoazaanthracene, 5,-monoazaanthracene, 1,2-diazaanthracene, 1,3-diazaanthracene, 1,4-diazaanthracene, 1,5-diazaanthracene, 1,6-diazaanthracene,1,7-diazaanthracene, 1,8-diazaanthracene, 1,9-diazaanthracene, 1,10-diazaanthracene, 2,3-diazaanthracene, 2,5-diazaanthracene, 2,7-diazaanthracene, 2,8-diazaanthracene and 5,10-diazaanthracene. In preferred embodiments of the invention, the planar ring system of the DNA intercalator is a 1,5-diazaantracene (aka benzo(b)-1,5-nathyridine), or a derivative thereof.

In preferred embodiments of the invention, the planar ring system of the DNA intercalator is an anthracene, a diazaantracene, or, more preferably, a 1,5-diaza-antracene with one or more substituents selected from the group consisting of —O$^{(-)}$, —OH, —OR, —OC$_6$H$_5$, —OCOCH$_3$, —NH$_2$, —NR$_2$, —NHCOCH$_3$, —R, —C$_6$H$_5$, —NO$_2$, —NR$^{(+)}$, —PR$^{(+)}$, —SR$^{(+)}$, —SO$_3$H, —SO$_2$R, —CO$_2$H, —CO$_2$R, —CONH$_2$, —CHO, —COR, —CN, —F, —Cl, —Br, —I, —CH$_2$Cl, —CH=CHNO$_2$, wherein R is any alkyl group.

The protein ligand may be any molecule that binds and interferes with the activity of a protein, and may hinder any signalling pathway involving said protein. It would be understood that communication within and between cells occurs via the transmission of signals through signalling pathways (also known as signal transduction). In preferred embodiments of the invention, the protein ligand binds a protein that is involved in a signalling pathway that leads to, or enhances/allows the progression of, cancer. This signalling pathway may be any pathway that results in any phenotype(s) associated with cancer, including but not limited to, cellular proliferation, cellular evasion of apoptosis and/or necrosis, cellular evasion of the immune response, incorporation and propagation of DNA damage, increased cellular motility and increased cellular metabolism. By hindering a signalling pathway that results in a phenotype associated with cancer, the protein ligand may assist in the treatment or prevention of cancer by reducing, minimizing, reversing, preventing, retarding or ablating the phenotype, or any effect of the phenotype, associated with cancer.

The protein ligand may hinder a signalling pathway by binding a protein and preventing a post-translational modification of the protein, such as specific cleavage reactions, the formation of disulphide bonds, the addition of low molecular weight groups via, for example, acetylation, amidation, biotinylation, cysteinylation, deamidation, formylation, glutathionylation, glycation, glycosylation, hydroxylation, methylation, oxidation, palmitoylation, or phosphorylation and/or conjugations with other types of molecules. In other examples, a signalling pathway may be hindered by the protein ligand binding a protein and preventing the removal of low molecular weight groups added by any of the foregoing post-translational processes.

The skilled addressee would appreciate that one of the most commons cellular mechanisms of signal transduction is protein phosphorylation by kinases and protein dephosphorylation by phosphatases. Accordingly, in preferred embodiments of the invention, the protein ligand hinders a signalling pathway that leads to, or enhances/allows the progression of, cancer, by interfering with the phosphorylation state of a protein in the signalling pathway. By interfering is meant that (a) the protein ligand may bind a protein in the signalling pathway and prevent or allow phosphorylation or dephosphorylation of that protein; or (b) the protein ligand may bind a protein in the signalling pathway and prevent or allow that protein from phosphorylating or dephosphorylating other substrates in the signalling pathway.

A particularly common characteristic of cancer is the increased activity, overexpression or loss of negative regulation of protein kinases, which may be collectively referred to as the upregulation of protein kinases. In preferred embodiments of the invention, the protein ligand binds a protein kinase, and more preferably, the protein ligand binds a protein kinase that is involved in a signalling pathway that leads to, or enhances/allows the progression of, cancer. The protein ligand may bind the protein kinase and prevent, perturb or reduce the ability of the protein kinase to phosphorylate targets involved in the signalling pathway. The action of the protein kinase may be prevented, perturbed or reduced by the binding of the protein ligand temporarily, reversibly, permanently or in response to particular stimuli. The action of the protein kinase may be prevented, perturbed or reduced by the binding of the protein ligand by, for example, the protein ligand inducing conformational changes in the protein kinase, the protein ligand occupying binding sites on the protein kinase, the protein ligand blocking other receptor sites that would ordinally trigger phosphorylation events and/or the protein ligand creating steric hindrance to the activity of the kinase. Accordingly, the protein ligand may be referred to as a protein kinase inhibitor.

The protein ligand may bind and inhibit any protein kinase that is upregulated in a signalling pathway that leads to, or enhances/allows the progression of, cancer. In certain embodiments of the invention, the protein kinase is a kinase involved in the MAP (mitogen activated protein) kinase pathway (also known as the Ras/MAPK pathway, or Ras/Raf/MAPK pathway or MAP/Erk pathway or Ras/Raf/Mek/Erk pathway), which is involved in cellular proliferation, cell survival and metastasis. In particular, the protein ligand may bind and inhibit a MEK (MAPK/Erk kinase), may bind an inhibit a Raf kinase, or may bind and inhibit an ERK (extracellular receptor kinase), or isoforms thereof.

In other embodiments, the protein ligand binds a protein kinase in the PI3K/Akt (phosphoinositide 3-kinase/Protein Kinase B) kinase pathway, which is a combination of many individual pathways involved in cellular proliferation, metabolism, cell survival, and DNA damage response. In particular, the protein ligand may bind and inhibit PI3K, Akt, PDK1, GSK-3, Wee1, Myt1, CHK1, CHK2, ATR, ATM, mTOR, CDK2 or PIP5K, or isoforms thereof.

In a further example, the protein ligand binds a protein kinase in the RIPK3/RIPK1 (Receptor interacting serine/threonine kinase 3/1; also known as RIP1 and/or RIP3 kinase pathway) kinase pathway, which in involved in apoptosis and necroptosis. In particular, the protein ligand may bind and inhibit RIPK3, RIPK1, TAK1 or FADD, or isoforms thereof. In other examples, the protein ligand binds and inhibits PKC (Protein kinase C) or isoforms thereof, which is involved in cellular proliferation, motility and survival.

In embodiments of the present invention, the protein ligand is a protein kinase inhibitor, wherein the protein kinase is selected from the group consisting of MEK, Raf, ERK, PI3K, Akt, PDK1, GSK-3, Wee1, Myt1, CHK1, CHK2, ATR, ATM, mTOR, CDK2, PIP5K, RIPK3, RIPK1, TAK1, FADD and PCK, and/or isoforms thereof.

The protein ligand may bind more than one protein kinase. Accordingly, in embodiments of the present invention, the protein ligand binds and inhibits one or more protein kinases selected from the group consisting of MEK, Raf, ERK, PI3K, Akt, PDK1, GSK-3, Wee1, Myt1, CHK1, CHK2, ATR, ATM, mTOR, CDK2, PIP5K, RIPK3, RIPK1, TAK1, FADD and PCK, and/or isoforms thereof.

In embodiments of the present invention, the protein ligand binds the kinase, Glycogen Synthase Kinase-3 (GSK-3), and may be referred to as a GSK-3 ligand. In this instance, the protein ligand may be any molecule that binds to GSK3α and/or GSK3β, wherein it is understood that GSK3α and GSK3β are paralogs that have different and overlapping phosphorylation substrates, and respond to different and overlapping molecular signals. For ease of reference, both molecules will be collectively referred to as GSK-3, though it would be understood the GSK-3 ligand may preferentially bind one of the paralogs, may bind the paralogs with different specificities and affinity, and/or may preferentially bind one of the paralogs, for example, in particular cellular locations, in response to different stimuli and/or when being used in the treatment or prevention of different cancers. Alternatively, the GSK-3 ligand may bind each of the paralogs at the same site with similar specificity and affinity.

GSK-3 is a prolific and promiscuous kinase, known to be involved in tumour promotion via increased cellular metabolism and the formation of anti-apoptotic protein complexes. GSK-3 is present throughout the cell, including in the nucleus. Accordingly, without wishing to be bound by theory, it is proposed that the interference of GSK-3 signalling in proliferating cells, such as cancerous cells, can disrupt many relevant cellular processes, thereby slowing or stopping cellular proliferation and/or encouraging cell death.

In one or more embodiments, the protein ligand may comprise one or more aromatic 5- or 6-membered rings, wherein the ring(s) may be substituted and/or heterocyclic. In other embodiments, the protein ligand may comprise 5- or 6-membered rings that are not aromatic, and the rings may be substituted at any one of the atoms in the ring structure. In embodiments of the invention, the protein ligand may comprise one or more benzene or phenyl rings, and these may be halogenated, nitrated, sulfonated, alkylated, acylated and/or substituted with sterically permissible combinations thereof. In further embodiments, the protein ligand may comprise one or more pyrrolidine rings. The protein ligand may comprise one or more aromatic 6-membered rings and/or one or more 5-membered rings, with one or more substituents selected from the group consisting of $-O^{(-)}$, $-OH$, $-OR$, $-OC_6H_5$, $-OCOCH_3$, $-NH_2$, $-NR_2$, $-NHCOCH_3$, $-R$, $-C_6H_5$, $-NO_2$, $-NR_3^{(+)}$, $-PR_3^{(+)}$, $-SR_2^{(+)}$, $-SO_3H$, $-SO_2R$, $-CO_2H$, $-CO_2R$, $-CONH_2$, $-CHO$, $-COR$, $-CN$, $-F$, $-Cl$, $-Br$, $-I$, $-CH_2Cl$, $-CH=CHNO_2$, $-C_2H_5$, $-CR_2H$, $-CR_3$, wherein R is any alkyl group. In preferred embodiments, the protein ligand may comprise a phenyl ring and one or more pyrrolidine rings, the phenyl ring and/or the pyrrolidine ring may be substituted with one or more substituents selected from the group consisting of $-O^{(-)}$, $-OH$, $-OR$, $-OC_6H_5$, $-OCOCH_3$, $-NH_2$, $-NR_2$, $-NHCOCH_3$, $-R$, $-C_6H_5$, $-NO_2$, $-NR^{(+)}$, $-PR^{(+)}$, $-SR_2^{(+)}$, $-SO_3H$, $-SO_2R$, $-CO_2H$, $-CO_2R$, $-CONH_2$, $-CHO$, $-COR$, $-CN$, $-F$, $-Cl$, $-Br$, $-I$, $-CH_2Cl$, $-CH=CHNO_2$, $-C_2H_5$, $-CR_2H$, $-CR_3$, wherein R is any alkyl group.

The protein ligand may bind or interact with the protein at particular residues. These residues may, for example, be part of one or more binding or phosphorylation sites on the protein. Alternatively, the residues may be crucial for protein docking or phosphorylation of a protein substrate.

In embodiments of the invention, the protein ligand may bind or interact with specific residues on GSK-3. For example, the GSK-3 ligand may bind a GSK-3β active site via hydrogen bonding to Valine 135, Glutamine 185, and via van der Waals interactions to several additional amino acids.

In the methods of the present invention, the cancer may be treated or prevented by administering a composition comprising a DNA ligand and a protein ligand, wherein the ligands are separate molecules. This would allow the composition to comprise different molar ratios of the two ligands, and allow the ligands to localise in different parts of the cell, and/or to co-localise. For example, the composition may comprise an excess of DNA ligand (i.e., a molar ratio of DNA ligand:protein ligand of 1000:1 to 1.1:1), or an excess of protein ligand (i.e., a molar ratio of DNA ligand: protein ligand of 1:1000 to 1:1.1), or equal molar amounts of DNA ligand and protein ligand. The ratio of the DNA ligand and protein ligand may be modified and tailored depending on factors such as the type of cancer being treated, the stage of cancer, the subject's age and overall health and sensitivity to the effects of the DNA ligand and/or protein ligand.

In other embodiments, the DNA ligand and protein ligand are separate molecules that are conjugated together, which would typically be in a 1:1 ratio, though the ligands may be conjugated in such a way as to allow an excess of the DNA ligand or the protein ligand. For example, 1-10 molecules of the DNA ligand may be conjugated to a single protein ligand, or 1-10 molecules of the protein ligand may be conjugated to a single DNA ligand. By conjugation is meant that the DNA ligand and protein ligand are manufactured separately and linked by an appropriate and pharmaceutically acceptable spacer or cross-linker, or by electrostatic or covalent interactions, for administration at a set ratio. The spacer or cross-linker may be cleavable under certain stimuli, or the conjugation may be irreversible.

In preferred embodiments of the invention, the DNA ligand and protein ligand are components of a single compound. The DNA ligand and the protein ligand may be joined by any appropriate linker in a single compound. The linker may be rigid or flexible and/or may be of any length that facilitates the DNA ligand being able to bind DNA and the protein ligand being able to bind the protein. The linker need not allow for simultaneous binding of DNA and the protein, though this is preferred in some embodiments. The linker may comprise an amine group. The compound may comprise other ligands and/or active site.

In the event the DNA ligand and the protein ligand are conjugated or part of a single compound, it would be understood this would result in the DNA ligand and protein ligand co-localising. At any given time, the compound or conjugated ligands may be localised such that only the DNA ligand or only the protein ligand may be capable of binding DNA or the protein, respectively. Alternatively, the compound or conjugated ligands may be localised such that both the DNA ligand and the protein ligand are capable of binding their respective target molecules simultaneously. The ability of the DNA ligand and the protein ligand in the compound or the conjugated ligands to bind DNA and protein, respectively, either simultaneously or sequentially can fluctuate over time or in response to cellular activities.

In preferred embodiments, the DNA ligand and protein ligand are in the form of pyronaridine (PND), or a derivative or pharmaceutically acceptable salt thereof. Pyronaridine has the chemical formula $C_{29}H_{32}ClN_5O_2$, and the chemical name, 4-[(7-chloro-2-methoxy-1,5-dihydrobenzo[b][1,5]naphthyridin-10-yl)imino]-2,6-bis(pyrrolidin-1-ylmethyl)cyclohexa-2,5-dien-1-one (previously, 2-methoxy-7-chloro-10-(3',5'-bis(pyrrolin-1-ylmethyl)-4'-hydroxyphenylamino)benzo(b)-1,5-naphthyridine). Pyronaridine is also known as malaridine and benzonaphthyridine 7351.

In therapeutic applications, pyronaridine is preferably used as a phosphate salt, or a pyronaridine tetraphosphate, which has the chemical formula, $C_{29}H_{44}ClN_5O_{18}P_4$, and chemical name 4-[(7-chloro-2-methoxy-1,5-dihydrobenzo[b][1,5]naphthyridin-10-yl)imino]-2,6-bis(pyrrolidin-1-yl-methyl)cyclohexa-2,5-dien-1-one; phosphoric acid.

Pyronaridine tetraphosphate is a common antimalarial agent that has been approved and used effectively for the treatment of malaria for over 30 years. In recent times, it has been found to enhance the antitumor activity of some common chemotherapeutic drugs when targeting multi-drug resistant cancers, though it has never been used alone in the treatment or prevention of cancer in in vivo studies, nor has it been suggested as a stand-alone anti-cancer therapy that can target proliferating cells. Surprisingly, it has been found by way of the present invention that pyronaridine is an effective anti-cancer agent with a DNA ligand and a protein ligand. Despite the compound having two therapeutic targets, it is generally well tolerated and safe to use. Without wishing to be bound by theory, it is hypothesised the pyronaridine selectively targets proliferating cancer cells for apoptosis and interferes with molecular mechanisms that may ordinarily allow cancer cells to evade cell death. That the pyronaridine is selective in targeting proliferating cells is important as it reduces the side-effects which are commonly associated with less selective cancer treatments.

Pyronaridine comprises a DNA binding ligand that is an anthracene derivative of three fused benzene rings, and a protein ligand that comprises a 6-membered aromatic ring and two 5-membered rings. In pyronaridine, the DNA binding ligand is a substituted 1,5-diaza-antracene, though in embodiments of the invention the method relies on a pyronaridine derivative that may have alternative substituents at alternative positions on the rings' structures. In other derivatives of pyronaridine, the DNA ligand is a heterocyclic anthracene derivative with nitrogen present in different positions in the rings' structures of the fused aromatic rings. It is proposed that this structural aspect of pyronaridine (i.e., the planar nature of the three fused benzene rings) allows the DNA ligand of pyronaridine to act as a DNA intercalator to contribute to the initiation of apoptosis.

This feature is in contrast to other antimalarial agents that have been suggested to enhance the activity of chemotherapeutic agents against resistant cell lines, such as amodiaquine, mefloquine, naphthoquine, pamaquine, primaquine, piperaquine, tafenoquine, mepacrine, halofantrine, pyronaridine, nitazoxanide, and atovaquone. It is possible the lack of structural similarity between pyronaridine and these agents accounts for the different functionality of pyronaridine (i.e., treating cancer alone) when compared to the other antimalarial agents (i.e., enhances the treatment of cancer in resistant cells by inhibiting autophagy).

In pyronaridine, the protein binding ligand comprises a phenyl group, though in embodiments of the invention, the method relies on a pyronaridine derivative that may have alternative substituents at alternative positions on the benzene ring. In other derivatives of pyronaridine, the protein ligand comprises a heterocyclic 6-membered ring. In pyronaridine, the protein binding ligand further comprises 2 pyrrolidine rings, though in embodiments of the invention the method relies on a pyronaridine derivative that may have one or more substituted pyrrolidine rings, and/or may comprise aromatic 5-membered rings, or 5-membered rings with other molecules besides carbon and nitrogen in the ring structure.

In other preferred embodiments of the invention, the method comprises administering to a subject in need thereof a composition comprising pyronaridine tetraphosphate.

In the method of the invention, the cancer may be any cancer that presents as a solid tumour or a blood (liquid) cancer including, but not limited to, sarcomas, carcinomas, lymphomas, leukemia, myelomas and circulating tumour cells (CTCs). For example, the carcinoma may be that of the pancreas, bladder, breast, colon, mesothelioma, kidney, liver, lung, including small cell lung cancer, non-small cell lung cancer, head and neck, oesophagus, gall bladder, ovary, stomach, cervix, thyroid, prostate or skin. In general, the cancer will be characterized by uncontrolled cellular proliferation.

In other examples, the lymphoma may be B-cell lymphoma, T-cell lymphoma, Hodgkins lymphoma, non-Hodgkins lymphoma, hairy cell lymphoma, mantle cell lymphoma, myeloma, Burkett's lymphoma, or an extranodal lymphoma of the stomach, breast or brain.

The sarcoma may, for example, be fibrosarcoma, rhabdomyosarcoma, chondrosarcoma, leiomyosarcoma, mesothelial sarcoma, angiosarcoma, liposarcoma, bone tumours and tumors of the central and peripheral nervous system, including astrocytoma, neuroblastoma, glioma and schwannomas, or other tumors, including melanoma, seminoma, teratocarcinoma, osteosarcoma, xenoderoma pigmentosum, keratoctanthoma, thyroid follicular cancer and Kaposi's sarcoma.

The myeloma may be, for example, plasma cell myeloma or Kahler's disease or multiple myeloma. In other examples, the leukemia may be myelogenous leukemia, granulocytic leukemia, lymphatic leukemia, lymphocytic leukemia or lymphoblastic leukemia, polycythemia vera or erythremia.

In other non-limiting examples, the cancer may be, for example, acute lymphoblastic leukemia, acute myeloid leukemia, adrenocortical carcinoma, HIV and AIDS-related cancers, primary CNS lymphoma, anal cancer, gastrointestinal carcinoid tumors, brain astrocytomas, atypical teratoid/rhabdoid tumors, basal cell carcinoma, bile duct cancer, ewing sarcoma. osteosarcoma, malignant fibrous histiocytoma, brain glioma, bronchial tumors, cardiac tumors, embryonal tumors, germ cell tumors, cholangiocarcinoma, chordoma, chronic lymphocytic leukemia, chronic myelogenous leukemia, chronic myeloproliferative neoplasms, colorectal cancer, craniopharyngioma, cutaneous T-cell lymphoma, mycosis fungoides, Sézary syndrome, ductal carcinoma in situ (DCIS), uterine cancer, ependymoma, esthesioneuroblastoma, extragonadal germ cell tumors, eye cancer, intraocular melanoma, retinoblastoma, fallopian tube cancer, gastric cancer, gastrointestinal stromal tumors, testicular cancer, hypopharyngeal cancer, lip, mouth and oral cavity cancer, male breast cancer, merkel cell carcinoma, midline tract carcinoma with NUT gene changes, multiple endocrine neoplasia syndromes, myelodysplastic syndromes, nasal cavity and paranasal sinus cancer, nasopharyngeal cancer, oropharyngeal cancer, pancreatic neuroendocrine tumors, papillomatosis, paraganglioma, parathyroid cancer, penile cancer, pharyngeal cancer, pheochromocytoma, pituitary tumors, pleuropulmonary blastoma, primary peritoneal cancer, salivary gland cancer, vascular tumors, urethral cancer, uterine sarcoma, vaginal cancer, vulvar cancer, and Wilms tumor.

The methods of the present invention may prevent, delay or retard the development of cancers that, for example, may ordinarily develop from the metastasis of any of the cancers mentioned above. The methods may also prevent, delay or retard the recurrence of any of the cancers mentioned above after treatment.

The cancer may also be any cancer wherein the proliferative capacity of the cancer cells is modulated by protein in any way. In some embodiments, the cancer may be any cancer wherein the cancer cells overexpress protein. It would be understood that by "overexpress" is meant that the cancer cell expresses more protein than a healthy cell of the same tissue or cell type. For example, a cancerous cell present in a breast tumour would be considered to overexpress protein if, when compared to a non-cancerous breast tissue cell, the expression level of protein in the cancerous cell present in a breast tumour was greater. Expression levels of protein in a cell may be determined by the skilled addressee using well known techniques, such as, but not limited to, mRNA quantitation, immunofluorescence and western blotting.

While the composition of the invention may be used alone for effectively treating and preventing cancer, in some embodiments of the invention, the method comprises administering to a subject in need thereof a composition comprising a DNA ligand and a protein ligand, and an additional bioactive agent. The bioactive agent may be included in the composition comprising the DNA ligand and protein ligand, or the bioactive agent may be co-administered with the composition comprising the DNA ligand and protein ligand. By co-administered is meant that the agent and composition may be administered at the same time, or the composition and the agent may be administered at, for example, alternating times, or in advance of each other, or in follow-up to each other, or combination thereof (i.e., pre-administration or post-administration is included in the meaning of the term co-administration). For example, the bioactive agent may be administered in advance of the composition, and also administered at the same time or for the same duration as the composition. By "same time" is not meant to be limited to an actual time, but rather a time-frame or duration. For example, a bioactive agent may be administered to a subject at the same time as a composition of the invention, whereby this means that the bioactive agent is administered according to any suitable schedule for a particular period (days, weeks, months or years), while the subject is also receiving a composition of the invention at the same or different schedule for the same particular period (i.e., the patient maybe be receiving a daily dose of the composition of the invention for three months, while, during that three months, the subject is receiving a weekly does of the bioactive agent).

The bioactive agent may be any compound having biological activity with respect to the cancer, including therapeutic activity. The bioactive agent may be capable of binding or interacting with the cells of the cancer. The bioactive agent may be any agent, drug, compound or composition that may be used for the detection, prevention and/or treatment of a cancer. In embodiments of the present invention, the bioactive agent is a therapeutic agent, and more preferably, a chemotherapeutic agent. In embodiments of the invention, the DNA ligand and protein ligand are in the form of pyronaridine (PND), or a derivative or pharmaceutically acceptable salt thereof, and the bioactive agent is included in the composition comprising pyronaridine, or the bioactive agent is co-administered with the composition comprising pyronaridine.

In particularly preferred embodiments of the invention, the bioactive agent is a chemotherapeutic agent selected from the group consisting of Abiraterone acetate, Albumin-bound (nab) paclitaxel, Alemtuzumab, Altretamine, Asparaginase, Bendamustine, Bevacizumab, bleomycin, Bortezomib, Brentuximab vedotin, Busulfan, Cabazitaxel, Capecitabine, Carboplatin, Carmustine, Cetuximab, Chlorambucil, Cisplatin, Cladribine, Crizotinib, Cyclophosphamide, Cytarabine (Ara-C), Dacarbazine, Dactinomycin, Dasatinib, Daunorubicin, DaunoXome (liposomal daunorubicin), DepoCyt (liposomal cytarabine), Docetaxel, Doxil (liposomal doxorubicin), Doxorubicin, Eribulin mesylate, Erlotinib, Estramustine, Etoposide, Everolimus, Floxuridine, Fludarabine, Fluorouracil, Gefitinib, Gemcitabine, Gliadel wafers, Hydroxyurea, Ibritumomab, Ibritumomab, Idarubicin, Ifosfamide, imatinib, Ipilimumab, Irinotecan, Ixabepilone, Lapatinib, Lenallidomide, Lomustine, Mechlorethamine, Melphalan, Mercaptopurine, Methotrexate, Mitomycin, Mioxantrone, MG132, Nilotinib, Oxaliplatin, Paclitaxel, Panitumumab, Pazopanib, Peginterferon alfa-2b, Pemetrexed, Pentostatin, Pralatrexate, Procarbazine, Rituximab, Romidepsin, Ruxolitinib, Sipuleucel-T, Sorafenib, Streptozocin, Sunitinib, Temozolomide, Temsirolimus, Teniposide, Thalidomide, Thioguanine, Thiotepa, Topotecan, Tositumomab, Trastuzumab, Valrubicin, Vandetanib, Vemurafenib, Vinblastine, Vincristine and Vinorelbine. The skilled addressee would understand that this is by no means an exhaustive list, and that other chemotherapeutic agents developed in the future may be suitable for use in the methods of the present invention.

In more preferred embodiments of the invention, the DNA ligand and protein ligand are in the form of pyronaridine (PND), or a derivative or pharmaceutically acceptable salt thereof, and a bioactive agent is included in the composition comprising pyronaridine, or a bioactive agent is co-administered with the composition comprising pyronaridine, wherein the bioactive agent is selected from the group consisting of cisplatin, gemcitabine, bortezomib and MG132.

In embodiments of the invention, the method comprises the administration of a composition comprising two or more bioactive agents.

In other preferred embodiments of the present invention, the DNA ligand, protein ligand and/or the additional bioactive agent is a prodrug. A prodrug is a drug derivative of an active drug that may be inert or have lower toxicity than the active drug, which may be processed to the active drug in vivo. The processing may occur by enzymatic of chemical means, and/or the processing may be triggered by biological signals, such as changes in pH, and/or in response to binding a cellular component.

In another aspect of the invention, there is provided the use of a DNA ligand and a protein ligand in the preparation of a medicament for the treatment or prevention of cancer.

COMPOSITIONS AND MEDICAMENTS, DOSAGES AND ADMINISTRATION

The compositions, compounds, and medicaments of the present invention can be administered by oral, topical or parenteral routes, including intravenous, intramuscular, intraperitoneal, and subcutaneous. They may be delivered by injection directly into a tumour. They may also be administered to organs, tissues and cells ex vivo.

For intramuscular, intraperitoneal, subcutaneous and intravenous use, the compositions and medicaments of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate.

For oral administration, the compositions of the invention will generally be provided in the form of tablets or capsules or as an aqueous solution or suspension. Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate and lactose. Corn starch and alginic acid are examples of suitable disintegrating agents. Binding agents may include starch and gelatine. The lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatine capsules in which the active ingredient is mixed with a solid diluent and soft gelatine capsules wherein the active ingredient is mixed with water or an oil such as peanut oil, liquid paraffin or olive oil.

For topical administration, the compositions of the invention will generally be provided in the form of liquid, lotion, emulsion, mousse, paste, cream, ointment, or gel, and may be useful for the treatment of prevention of skin cancers or cancer near the skin surface, such that the DNA ligand and protein ligand would be able to diffuse to affected cells. Compositions of the invention for topical administration also include pharmaceutically acceptable preservatives, humectants, emollient, moisturisers, consistency factors, chelating agents, excipients, diluents and colouring agents.

Effective doses of the compositions, compounds and medicaments used in the present invention may be ascertained by conventional methods, and will generally be dependent on the therapeutic agent used. The specific dosage level required for any particular subject will depend on a number of factors, including the severity of the condition being treated, the route of administration and the weight of the subject.

For example, 1 unit dose may include about 0.1 mg to about 10000 mg of a single compound comprising a DNA ligand and protein ligand, or alternative form(s), derivative(s), or salt(s) thereof, or combinations thereof, and/or source(s) thereof described in any aspect and/or example of the invention. In another example, the unit dose includes about 50 mg to about 10000 mg, about 100 mg to about 10000 mg, about 200 mg to about 10000 mg, about 500 mg to about 10000 mg, about 1000 to about 10000 mg, about 2000 mg to about 10000 mg, about 4000 mg to about 10000 mg, about 8000 mg to about 10000 mg, about 5 mg to about 1000 mg, about 10 mg to about 1000 mg, about 20 mg to about 1000 mg, about 50 mg to about 1000 mg, about 100 to about 1000 mg, about 200 mg to about 1000 mg, about 400 mg to about 1000 mg, about 800 mg to about 1000 mg, about 0.5 mg to about 100 mg, about 1 mg to about 100 mg, about 2 mg to about 100 mg, about 5 mg to about 100 mg, about 10 to about 100 mg, about 20 mg to about 100 mg, about 40 mg to about 100 mg, or about 80 mg to about 100 mg. Preferably, the unit dose includes about 25 mg, about 100 mg, about 200 mg, about 300 mg, about 400 mg, about 500 mg, about 600 mg, about 700 mg, about 800 mg, about 900 mg, or about 1000 mg of a single compound comprising a DNA ligand and protein ligand, or alternative form(s), derivative(s), or salt(s) thereof, or combinations thereof, and/or source(s) thereof described in any aspect and/or example of the invention.

In other examples, 1 unit dose may include about 0.1 mg to about 10000 mg of a DNA ligand and about 0.1 mg to about 10000 mg of a protein ligand, or alternative form(s), derivative(s), or salt(s) thereof, or combinations thereof, and/or source(s) thereof described in any aspect and/or example of the invention. In another example, the unit dose includes about 50 mg to about 10000 mg, about 100 mg to about 10000 mg, about 200 mg to about 10000 mg, about 500 mg to about 10000 mg, about 1000 to about 10000 mg, about 2000 mg to about 10000 mg, about 4000 mg to about 10000 mg, about 8000 mg to about 10000 mg, about 5 mg to about 1000 mg, about 10 mg to about 1000 mg, about 20 mg to about 1000 mg, about 50 mg to about 1000 mg, about 100 to about 1000 mg, about 200 mg to about 1000 mg, about 400 mg to about 1000 mg, about 800 mg to about 1000 mg, about 0.5 mg to about 100 mg, about 1 mg to about 100 mg, about 2 mg to about 100 mg, about 5 mg to about 100 mg, about 10 to about 100 mg, about 20 mg to about 100 mg, about 40 mg to about 100 mg, or about 80 mg to about 100 mg of a DNA ligand, and about 50 mg to about 10000 mg, about 100 mg to about 10000 mg, about 200 mg to about 10000 mg, about 500 mg to about 10000 mg, about 1000 to about 10000 mg, about 2000 mg to about 10000 mg, about 4000 mg to about 10000 mg, about 8000 mg to about 10000 mg, about 5 mg to about 1000 mg, about 10 mg to about 1000 mg, about 20 mg to about 1000 mg, about 50 mg to about 1000 mg, about 100 to about 1000 mg, about 200 mg to about 1000 mg, about 400 mg to about 1000 mg, about 800 mg to about 1000 mg, about 0.5 mg to about 100 mg, about 1 mg to about 100 mg, about 2 mg to about 100 mg, about 5 mg to about 100 mg, about 10 to about 100 mg, about 20 mg to about 100 mg, about 40 mg to about 100 mg, or about 80 mg to about 100 mg of a protein ligand. Preferably, the unit dose includes about 25 mg, about 100 mg, about 200 mg, about 300 mg, about 400 mg, about 500 mg, about 600 mg, about 700 mg, about 800 mg, about 900 mg, or about 1000 mg of a DNA ligand and about 25 mg, about 100 mg, about 200 mg, about 300 mg, about 400 mg, about 500 mg, about 600 mg, about 700 mg, about 800 mg, about 900 mg, or about 1000 mg of a protein ligand, or alternative form(s), derivative(s), or salt(s) thereof, or combinations thereof, and/or source(s) thereof described in any aspect and/or example of the invention.

The unit dose may be administered once, twice, three, four or five times daily, or may be administered every second or third day, or once every week, once every two weeks or once every four weeks.

In some embodiments, the compositions, compounds and medicaments may be administered to a subject in isolation or in combination with other additional bioactive agent(s). In such embodiments the administration may be simultaneous or sequential.

Typically, in treatment applications, the compositions, compounds and medicaments may be administered for the duration of the cancer. Further, it will be apparent to one of ordinary skill in the art that the optimal quantity and spacing of individual dosages can be determined by the nature and extent of the disease state or condition being treated, the form, route and site of administration, and the nature of the particular subject being treated. Optimum dosages can be determined using conventional techniques.

Some embodiments of the present invention may involve administration of the composition or medicament in multiple, separate doses. Accordingly, the methods of treatment and prevention described herein encompass the administration of multiple separated doses to a subject, for example, over a defined period of time.

The compositions and medicaments of this invention may also be useful in combination (administered together or sequentially) with one or more additional therapeutic treatments such as radiation therapy, and/or one or more additional therapeutic agents selected from the group consisting of different types of chemotherapy drugs, anti-tumour antibiotics, topoisomerase inhibitors, mitotic inhibitors, corticosteroids, targeted therapies, differentiating agents, hormone therapy and immunotherapy.

DEFINITIONS

Unless the context clearly requires otherwise, throughout the description and the claims, the words "comprise", "comprising" and the like are to be construed in an inclusive sense as opposed to an exclusive or exhaustive sense; that is to say, in the sense of "including, but not limited to".

The term "treatment", and the like, in the context of the present specification includes the alleviation of the symptoms associated with a cancer, cancer regression and/or remission. In certain embodiments a treatment will slow, delay or halt the proliferation of cancerous cells, or metastasis of a cancer, slow, delay or halt the increase in a tumour size that would ordinarily occur from the cellular proliferation within the tumour, prevent differentiation of a cell line, reduce tumour size, or reverse the progression of one or more tumours, at least temporarily. The treatment may cure the cancer, or delay morbidity. Hence, in the context of this invention the word "treatment" or derivations thereof when used in relation to a therapeutic application includes all aspects of a therapy, such as the alleviation of pain associated with the cancer being treated, alleviation of the severity of the cancer being treated, improvement in one or more symptoms of the cancer being treated, improvement in the overall well-being of the subject being treated. Use of the word "treatment" or derivatives thereof will be understood to mean that the subject being "treated" may experience any one or more of the aforementioned benefits. In general, the treatment may be related to the death of proliferating cells present in the cancer.

The term "prevention", and the like, in the context of the present specification refers to the prevention of the recurrence of all or some of the symptoms associated with a cancer after a remission of said cancer, as well as the prevention of the formation of one or more cancers due to, for example, the metastasis of a cancer. The prevention may prevent morbidity due to one or more cancers, or delay morbidity due to one or more cancers. In general, the prevention may be related to the death of proliferating cells that may cause a cancer or cause a cancer to spread or recur.

In the context of this specification the term "about" will be understood as indicating the usual tolerances that a skilled addressee would associate with the given value.

In the context of this specification, where a range is stated for a parameter it will be understood that the parameter includes all values within the stated range, inclusive of the stated endpoints of the range.

In the context of the present invention, the term "subject" refers to an animal, preferably a mammal, most preferably a human, who has experienced and/or exhibited at least one symptom associated with a cancer. Typically, the subject is an individual having cancer and is under the clinical care of a medical practitioner. The subject may be human or may be a non-human such that reference to a subject or individual means a human or a non-human, such as an individual of any species of social, economic or research importance including, but not limited to, members of the classifications of ovine, bovine, equine, porcine, feline, canine, primates, rodents, especially domesticated members of those classifications, such as sheep, cattle, horses and dogs. Further, as used herein, a "subject in need thereof" may additionally be a subject who has not exhibited any symptoms of a cancer, but who has been deemed by a physician, clinician or other medical profession to be at risk of developing cancer. For example, the subject may be deemed at risk of developing cancer (and therefore in need of prevention or preventive treatment) as a consequence of the subject's medical history, including, but not limited to, family history, pre-disposition, co-existing/contributory cancer.

In the context of the present invention, by "pharmaceutically acceptable excipient or diluent" is meant any excipient or diluent that is not biologically undesirable, i.e., the material may be incorporated into a pharmaceutical composition of the present invention and administered to a subject without causing any undesirable or undue biological effects, including but not limited to undesirable or undue toxicity, incompatibility, instability, irritation, allergic response and the like. In a preferred embodiment, the excipient or diluent is approved or approvable by a regulatory agency or body, (the regulatory agency or body being, for example, a Federal or State government), or listed in the U.S. Pharmacopoeia or other generally recognized pharmacopoeia for use in subjects.

BRIEF DESCRIPTION OF THE FIGURES

Embodiments of the invention will now be described, by way of example only, with reference to the accompanying figures, for which the legends are provided below:

FIG. 3. Transcriptome analyses of possible pathways activated by pyronaridine (PND) and target validation. (A) Sub-networks for the most up-regulated (marked squares) genes in response to PND treatment of MDA-MB-231 cells. Pearson correlation analysis of the transcriptional signature of PND compared to the signatures deposited in LINCS project. Compounds marked correlate with the effects of PND, wherein darker the fill, the better the correlation. (B)

SDS-PAGE analysis reveals that PND caused inhibition of the topoisomerase II activity in a dose-dependent manner. Lane 1, catenated kinetoplast DNA (kDNA); Lane 2, decatenated kDNA; Lane 3, linear kDNA; Lane 4, kDNA plus topoisomerase II; Lane 5, kDNA plus topoisomerase plus 5 µM of PND; Lane 6, kDNA plus topoisomerase plus 50 µM of PND; Lane 7, kDNA plus topoisomerase plus 500 µM of PND; Lane 8, kDNA plus topoisomerase II plus 1 mM etoposoide (Topo II inhibitor); Lane 9, kDNA plus topoisomerase ii plus PBS; 10, kDNA plus topoisomerase II plus DMSO.

Figure 4:
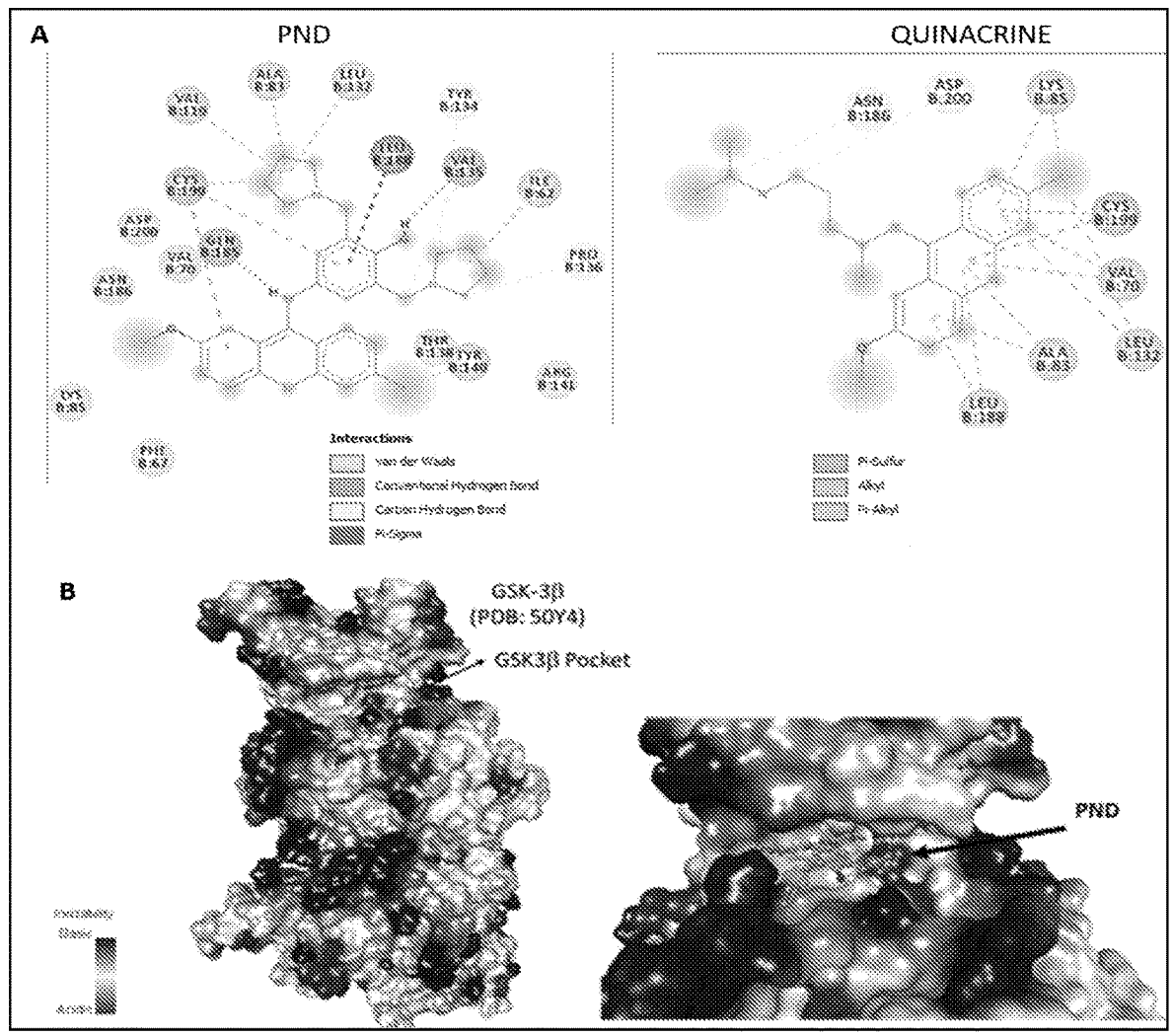

FIG. 4. Molecular docking studies of PND. Predicted interacting amino acid residues of PND and quinacrine on Glycogen Synthase Kinase 3β (A), and PND interacting specifically within the predicted binding pocket of GSK3β (B).

FIG. 5. PND Cytotoxic Concentration 50% ($CC_{50}$) and Selective Cytotoxic Index (SCI) on a panel of human cell lines. The SCI was calculated as follows: SCI=CC50 of non-cancerous cells/CC50 of cancer cells.

FIG. 6. Representative PND dose-response curves utilized to determine the CC50 values. For these analyses, cells were exposed for 72 h to PND and their viability was determined via the DNS assay. As an example, MDA-MB-231 (A) and HL-60 (B) were treated with a PND concentration gradient, as indicated on the x-axis; on the y-axis, the percentage of cytotoxicity (dead cells) is shown. In this series of experiments several controls were included: the diluent of PND, PBS, as contained in the experimental samples (0.5% v/v); as a negative control, untreated cells; and as a positive control of cytotoxicity, 1 mM $H_2O_2$. Each experimental point represents the mean of four replicas and error bars their corresponding standard deviation. Cytotoxic concentration 50% ($CC_{50}$) in micromolar (µM) units is defined as the concentration of PND required to disturb the plasma membrane of 50% of the cell population after 72 h of incubation.

Figure 7:
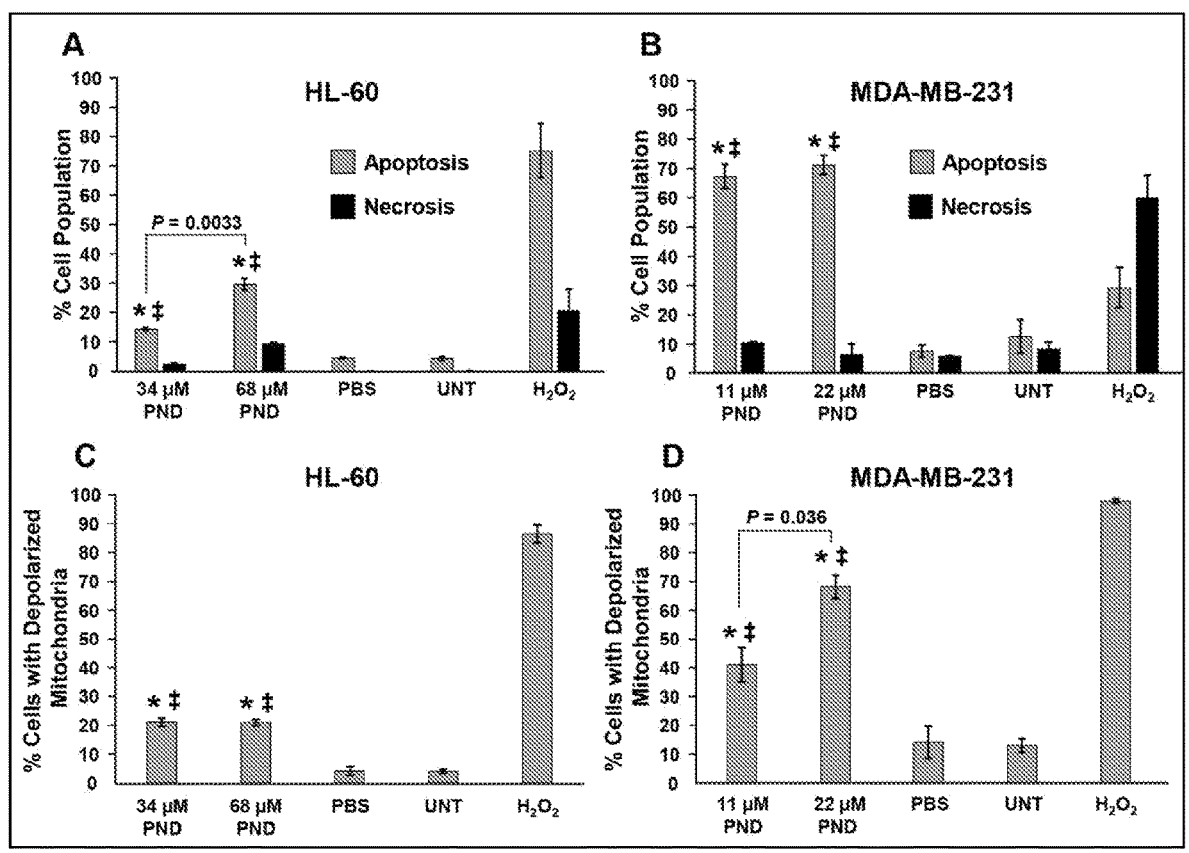

FIG. 7. PND caused phosphatidylserine externalization on MDA-MB-231 (A) and HL-60 (B) cancer cells after 24 h of incubation. The cell death mechanism was studied after double staining of cells with annexin V-FITC and PI and monitored via flow cytometer. (A-B) The total percentages of cell suffering apoptosis (y-axis) are expressed as the sum of both early and late stages of apoptosis (green bars); whereas cells stained only with PI, being annexin V-FITC negative, were counted as the necrotic cell population (black bars). Calculations of two-tailed Student's paired t-test of PND-treated cells as compared with PBS-treated (*) and untreated (‡) cells controls, provided consistently values of P<0.001, in both circumstances. Each bar represents the mean of triplicate, and error bars the standard deviation. PND inflicted its cytotoxic effect via mitochondrial membrane depolarization on MDA-MB-231 (C) and HL-60 (D) cells. Cells were treated with PND for 6 h and changes in the mitochondrial membrane potential (Δψm) were monitored by staining them with JC-1; an aggregate-forming lipophilic fluorochrome reagent and examined via flow cytometer. JC-1 reagent emits a green fluorescence signal after mitochondrial depolarization. (C-D) Percentages of cells radiating green fluorescence signal, y-axis, versus different treatments, x-axis, are depicted. As a disturber of mitochondrial membrane potential (Δψm) positive control, 1 mM of $H_2O_2$ was utilized. Each bar represents the means of three replicates and error bars the standard deviation. Furthermore, analyses of two-tailed Student's paired t-test of PND-treated cells, as compared with PBS-treated (*) and untreated (‡) cells controls, provided consistently values of P<0.01 and P<0.001, respectively.

Figure 8:
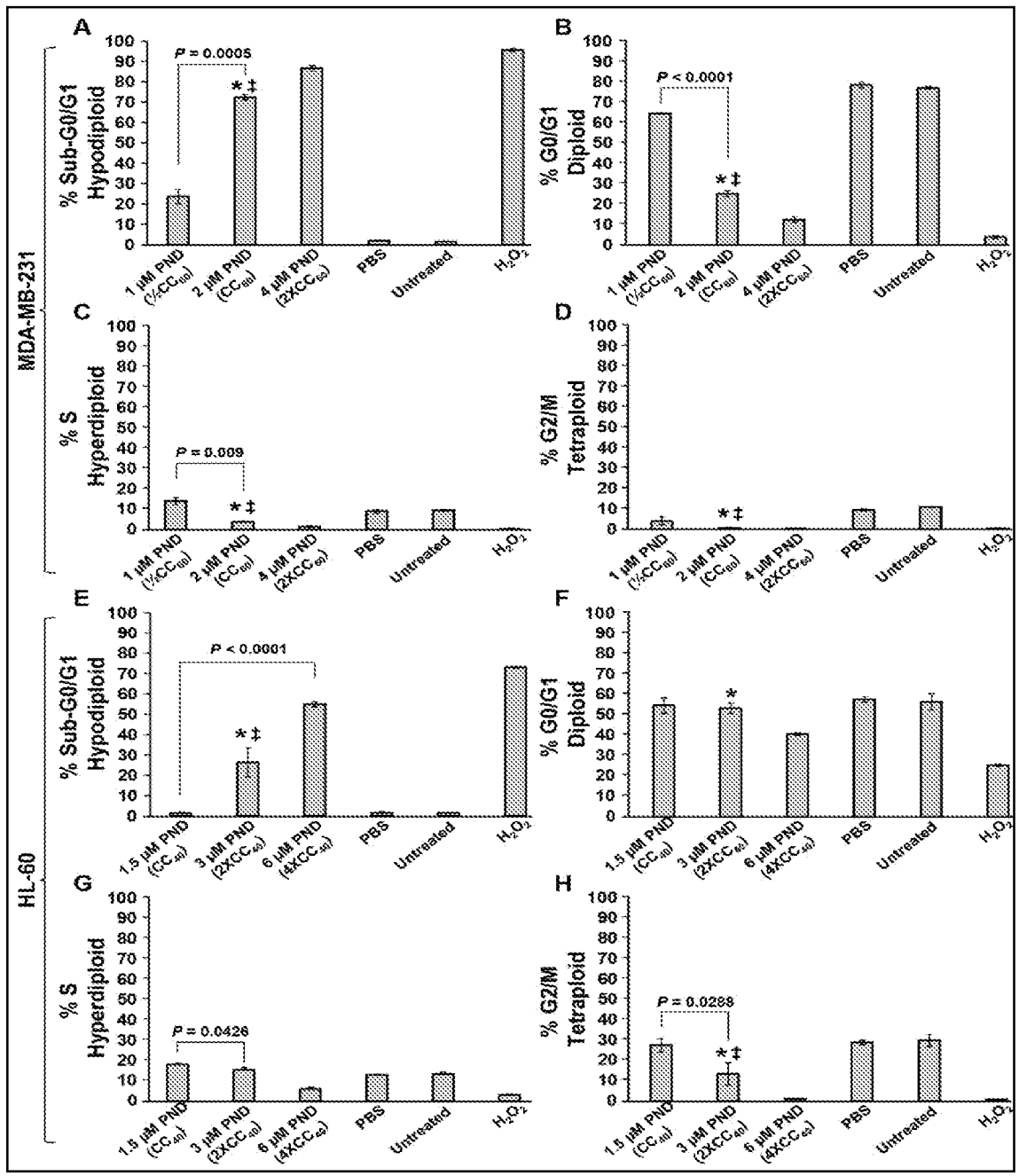

FIG. 8. PND disturbed the cell-cycle profile of two cancer cells, MDA-MB-231 (A-D) and HL-60 (E-H), and also exhibited apoptosis-induced DNA fragmentation in a dose-dependent mode. After 72 h of PND treatment, cells in 24-well culture plates were harvested, fixed, permeabilized, DAPI stained and analyzed via flow cytometer. The percentages for each cell cycle phases are presented along with the y-axis, whereas the different treatments are displayed along the x-axis. For this series of experiments, the following controls were involved: 1 mM of $H_2O_2$ was used as cell cycle perturbation agent; 0.1% PBS as a vehicle/solvent control; and untreated cells. Each bar denotes an average of three replicates, and the error bars indicate their corresponding standard deviation. For assay data acquisition and analysis purposes, the FL 9 detector, a single-cell gate and Kaluza flow cytometry software (Beckman Coulter) were utilized.

Figure 9:
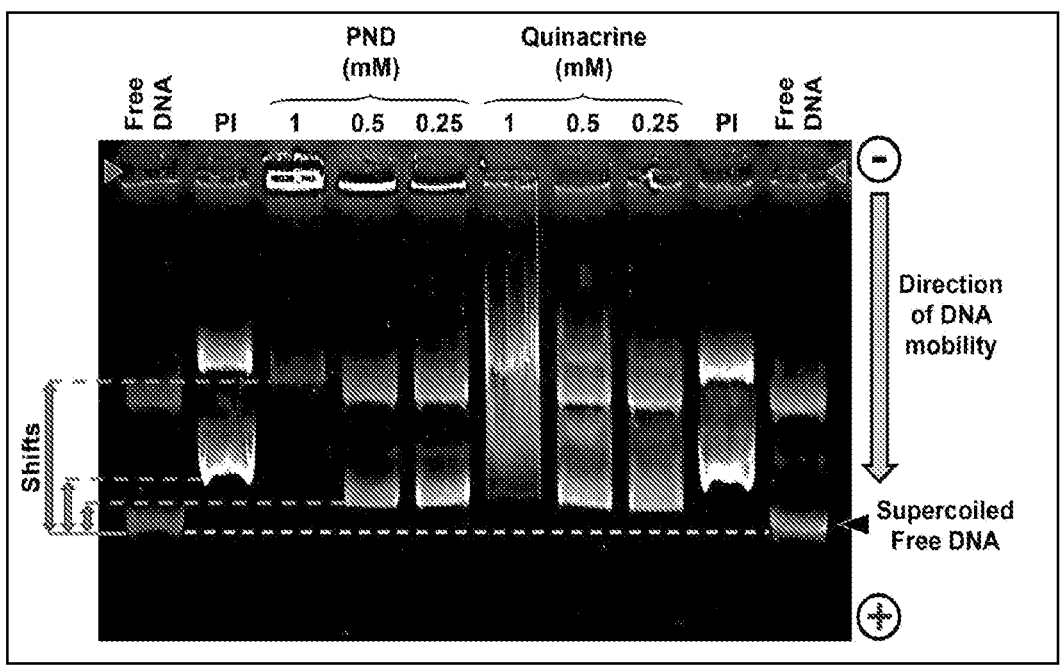

FIG. 9. PND provoked retardation of DNA migration in a dose-dependent manner. Three different concentrations of both PND and quinacrine were incubated individually with 100 ng of plasmid DNA and the potential of complexes formation was analyzed via an agarose gel electrophoresis. Reaction products were separated by 1% (w/v)-agarose-gel electrophoresis in Tris/acetate/EDTA buffer and stained with ethidium bromide. Both PI and free plasmid DNA were used as positive and negative controls of DNA mobility, respectively. The loading wells are located on the top of the image indicated by two blue head arrows (top left and right corners). The yellow dashed line is indicating the maximum mobility of the free supercoiled DNA used as a reference. Three DNA mobility-shifts are indicated by blue lines and arrows (left side of the image). Also, the migration direction of DNA is indicated by an arrow (right side of the image); from the cathode (negative) to the anode (positive). A representative image used to review the potential formation of DNA complexes is depicted.

Figure 10:
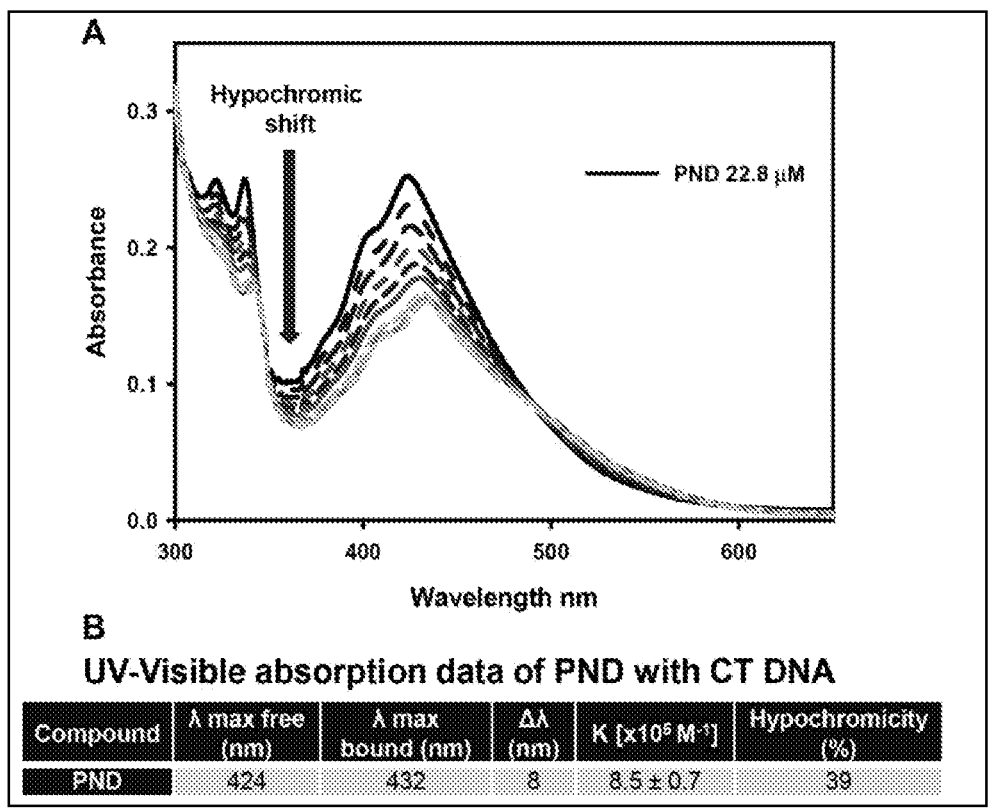

FIG. 10. Calf Thymus DNA caused a hypochromic and batochromic effect on PND maxima of absorbance. UV-Visible spectrophotometric titration (300-650 nm) of PND (22.8 µM) in Tris/HCl buffer upon consecutive additions of Calf Thymus (CT) DNA (10.1 mM). The arrow indicates the spectral changes when DNA is added. (B) Summary of the UV-Visible titration data from PND and CT DNA interaction.

Figure 11:
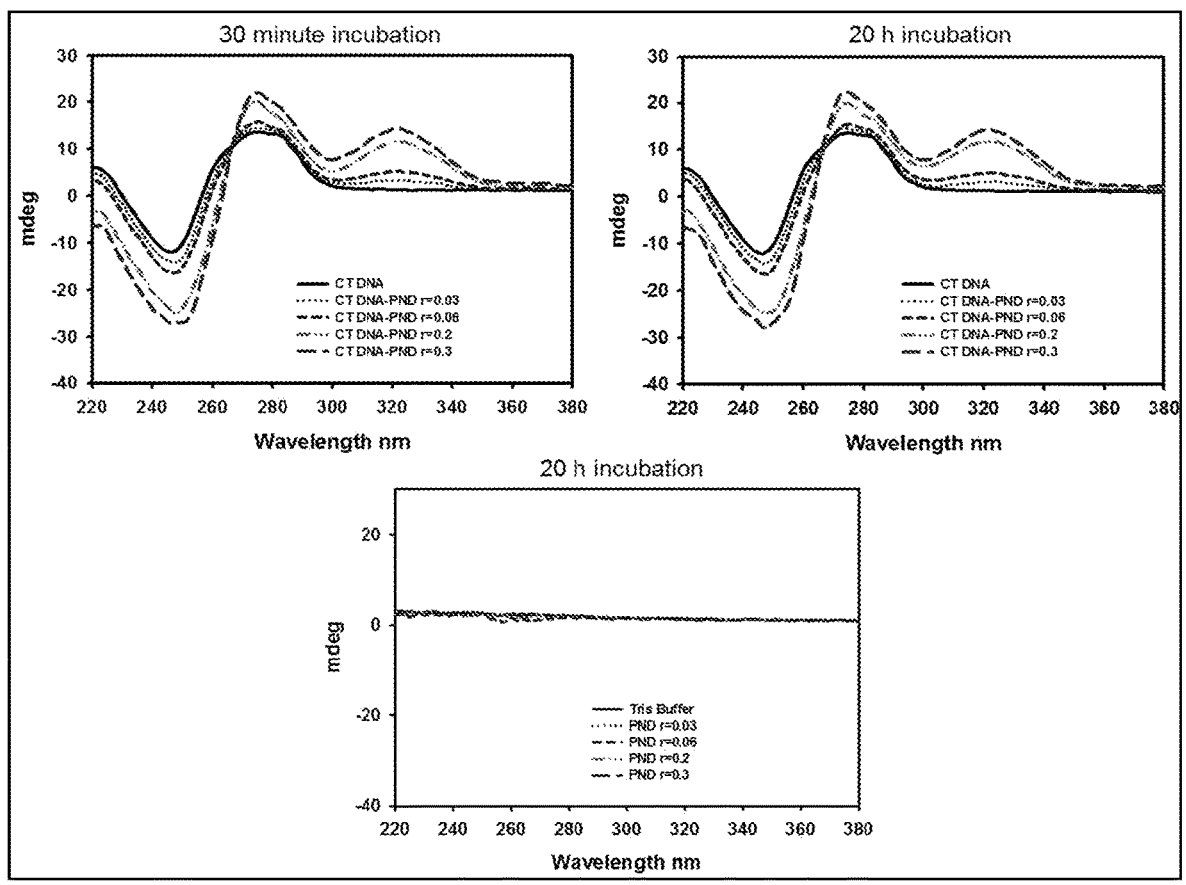

FIG. 11. PND induced an increase in the intensity of the positive and negative bands of the circular dichroism spectra of Calf Thymus DNA. Changes in the circular dichroism (CD) spectra of Calf Thymus (CT) DNA. CT DNA (150 µM) in Tris/HCl buffer was subjected to CD analysis after 30 min (A) or 20 h (B) of incubation with PND at molar ratios of 0.03, 0.06, 0.2 and 0.3. The arrows specify the CD spectral changes of CT DNA under a gradient of increasing PND concentrations. Blanks of CD spectra with the same gradient of PND concentrations in absence of CT DNA incubated for 20 h (C). Millidegrees=mdegs.

Figure 12:
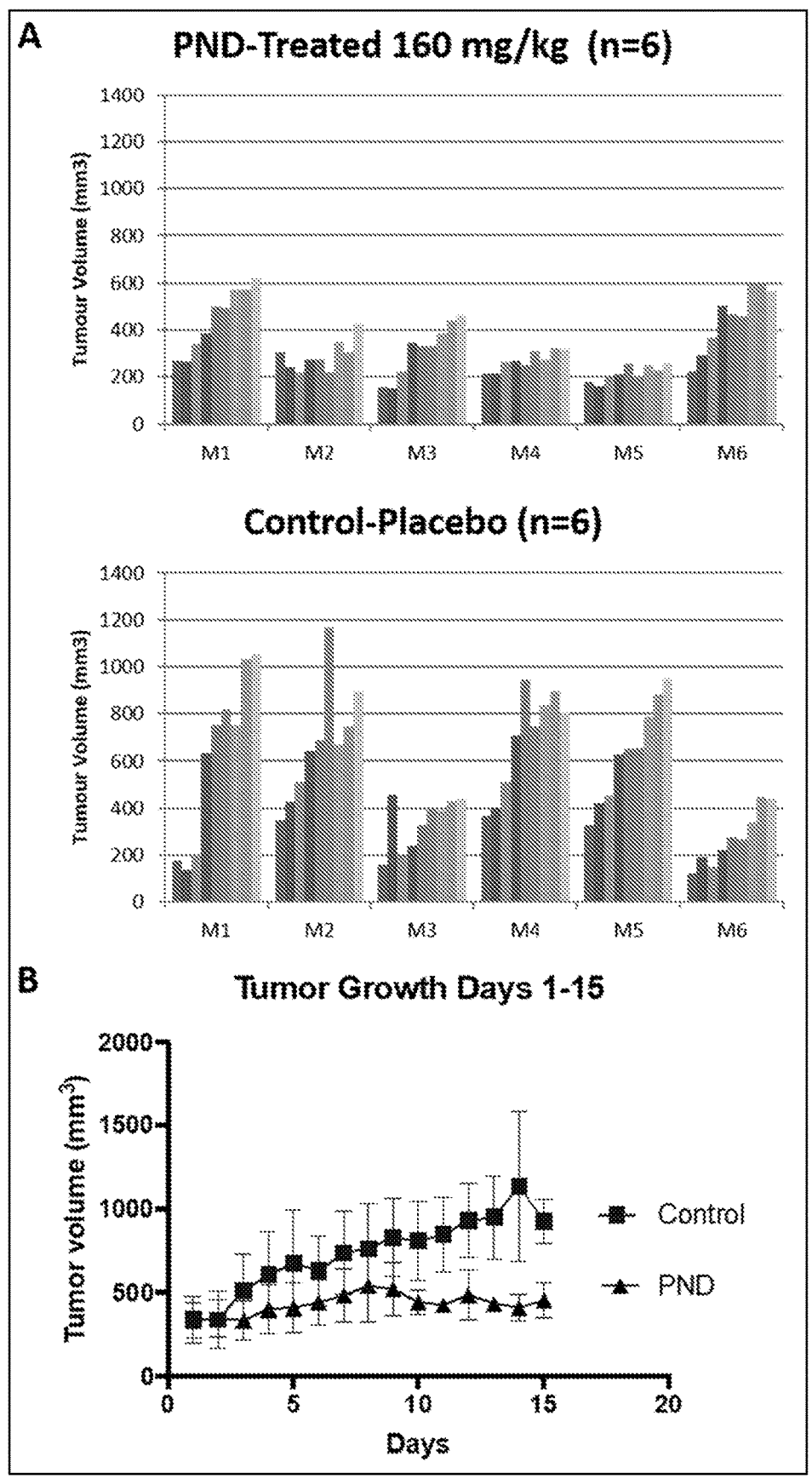

FIG. 12. PND treatment of mice resulted in a decrease in tumour growth. Metastatic breast cancer tumors grew on average larger in the control mice (750 mm$^3$) than in the PND-treated mice (430 mm$^3$), and the difference was significant from Day 1 to 15, t-test P-value of 0.01. In (A), the Days 1-9 are individual bars (left to right) for each mouse.

Figure 13:
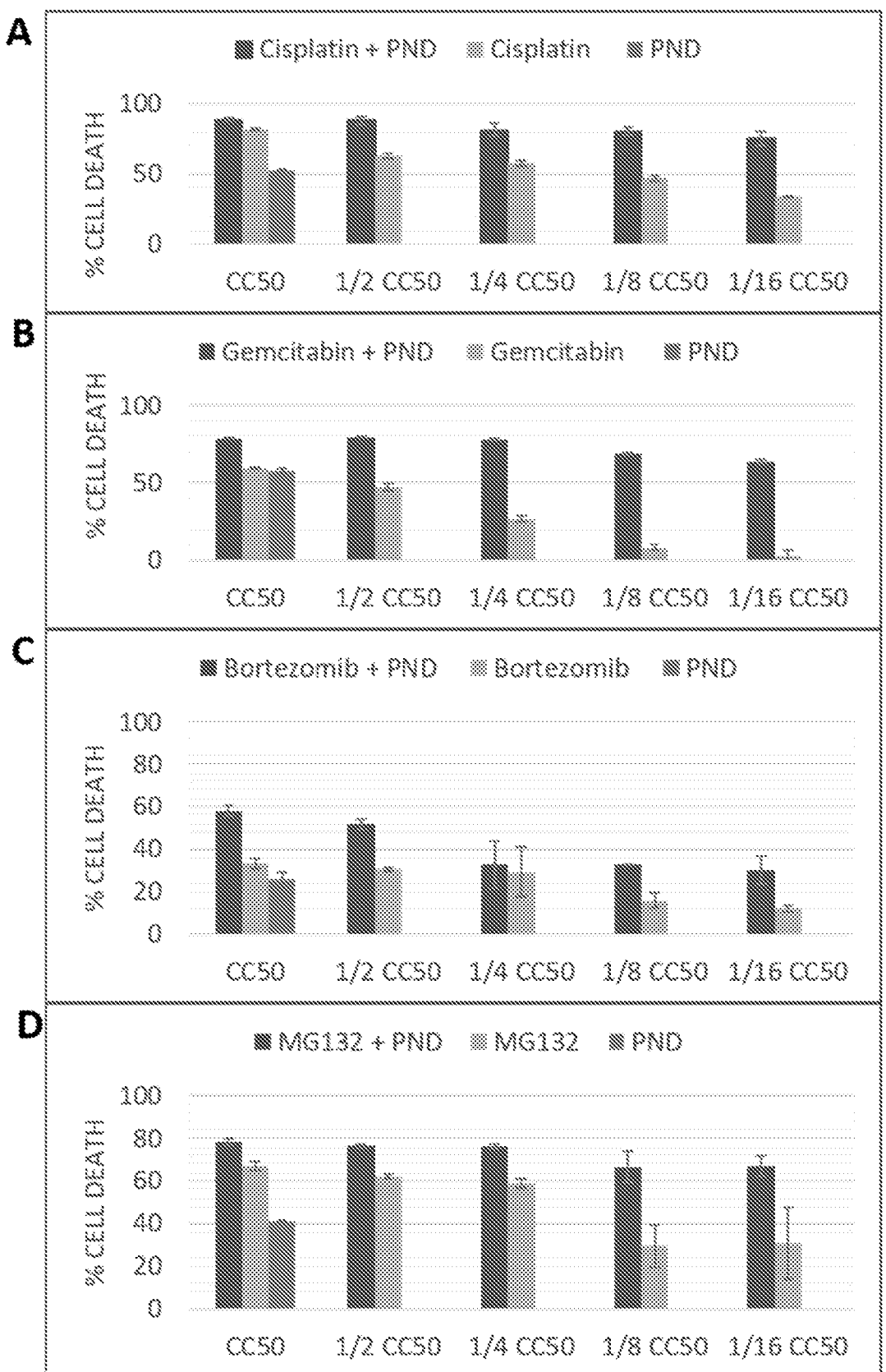

FIG. 13. PND treatment increases the activity of chemotherapeutic drugs at low doses on MDA-MB-231 breast cancer cell lines.

Example 1

Transcriptome Analysis

A transcriptome analysis was performed to compare the effects of PND with known drug signatures, using a range of different cell lines.

HL-60 cells (400,000 cells/2 ml/well in a 6-well plate) were treated with 5.6 µM, or PBS solvent control for 6 hours. RNA was extracted the following day and subjected to whole transcriptome analyses at the Genomic Analysis core facility of the University of Texas at El Paso. A total of three biological replicates were carried out for each treatment.

MDA-MB-231 cells were treated with PND ay double the CC50 concentration, or PBS solvent control, for 6 hours. RNA was extracted the following day and subjected to whole transcriptome analyses.

Figure 2:
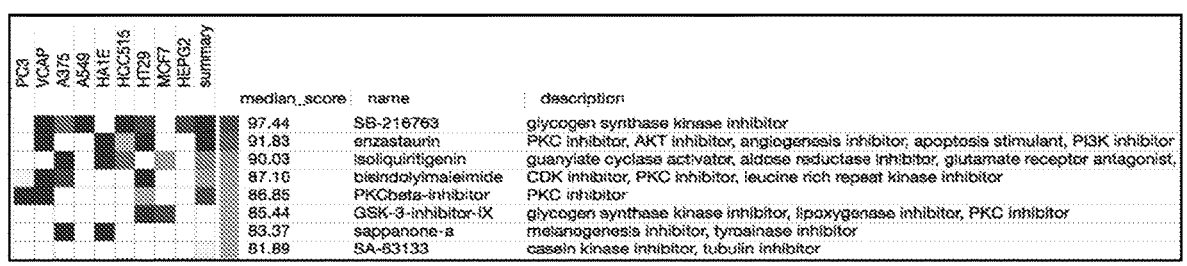
FIG. 2. Transcriptome analyses of possible pathways activated by pyronaridine (PND). Sub-networks for the most up-regulated (marked squares) genes in response to PND treatment of HL-60 cells. Pearson correlation analysis of the transcriptional signature of PND compared to the signatures deposited in LINCS project. Compounds marked correlate with the effects of PND, wherein darker the fill, the better the correlation.

In order to explore the possible Mechanism of Action (MoA) of PND, the transcriptome results for each cell line obtained were compared with the gene-expression data from the LINCS project (http://www.lincsproject.org), that contains the gene-expression profiles from various human cells treated with FDA-approved and withdrawn compounds as well as different well-characterized chemical reagents. It was reasoned that the expression profile of each lead compound should also induce a cellular gene expression response consistent with a known MoA of drugs deposited in LINCS. By using this approach, the signature of PND-treated cells was compared to each of the 476,251 genomic signature profiles in LINCS. The results shown in FIGS. 2 and 3A suggest PND may be a GSK inhibitor and topoisomerase inhibitor, respectively. The activity of PND as a Topoisomerase inhibitor was confirmed using a TopoGen Topoisomerase II Assay Kit, and the results can be seen in FIG. 3B.

Example 2

GSK-3 Docking

The crystal structure of GSK was obtained from the Protein Data Bank (5OY4) and used to model the interactions with PND and Quinacrine (see FIG. 4A). PND is shown to interact specifically within the predicted binding pocket of GSK3β (see FIG. 4B). Docking experiments were performed using GLIDE 5.0 within the Schrodinger Software package. Molecular docking studies have revealed that PND can interact within GSK3β with a high docking score (−9.4 Kcal/mol) while SB 216763 (from Example 1; see FIG. 2) had a similar score (−9.2 Kcal/mol)). Quinacrine showed low binding scores of −7.6 Kcal/mol, indicating that the side group of PND is likely providing additional contacts within the binding pocket (see FIG. 4A) that allow it to bind better to GSK-3.

Example 3

Analysis of PND Toxicity on Human Breast and Hematological Cancer Cells

The drug pyronaridine (PND) is a benzonaphthyridine derivative initially synthesized in 1970 at the Institute of Chinese Parasitic Disease and has been used in China for over 30 years for the treatment of malaria. Previous reports indicated that PND inhibits β-hematin formation promoting β-hematin-induced red blood cell lysis based on studies of *Plasmodium falciparum* K1 performed in vitro. In addition, PND has been previously tested in combination with doxorubicin (DOX) on multidrug-resistant (MDR) K562/A02 and MCF-7/ADR cancer cells and found to increase the sensitivity of cells to doxorubicin. However, it has never been determined or suggested PND had an effect by itself in the treatment of cancer.

Materials and Methods

Preparation of Pyronaridine Tetraphosphate-PND

Figure 1:
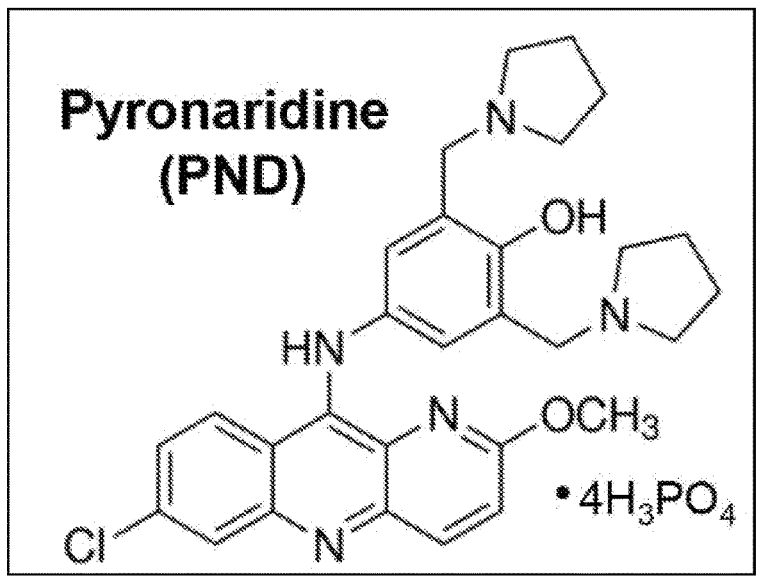
FIG. 1. The chemical structure of pyronaridine (PND) tetraphosphate.

Pyronaridine tetraphosphate (PND; 2-methoxy-7-chloro-10[3,5-bis(pyrrolidinyl-1-methyl-)4hydroxyphenyl]amino-benzyl-(b)-1,5-naphthyridine; APExBIO, Houston, TX, USA) stock solution and PND dilutions were freshly prepared by using Dulbecco's Phosphate Buffered Saline (PBS; Sigma-Aldrich, St Louis, MO, USA) as a solvent. Both the stock solutions and their dilutions were added directly to the wells containing cells in culture media. The chemical structure of pyronaridine tetraphosphate is depicted in FIG. 1.

Cell Lines and Culture Conditions

In this study, 19 human cell lines were utilized: seven breast human cancer; MDA-MB-468, MCF-7, T47D, HCC1419, HCC70, MDA-MB-231 (triple negative) and its lung metastatic (LM) derivative MDA-MB-231 LM2; four human leukemia/lymphoma cells, HL-60, Ramos, Jurkat and CEM, three human ovarian cancer, Ovcar 8, Ovcar 5 and Ovcar 3, one lung cancer, one melanoma and one pancreatic cell line, A549, A375, Panc-1 respectively. Furthermore, for selectivity/comparative purposes, the cell lines from the non-cancerous origin, MCF-10A, HS-27 were also included. The culture media used for MDA-MB-231, MDA-MB-231 LM2, MDA-MB-468, MCF-7, A549, A375, Panc-1, and HS-27 was DMEM (Hyclone, Logan UT), whereas for T47D, HCC-1419, HCC-70, HL-60, Ramos, Jurkat, CEM, Ovcar 8 and Ovcar 5 was RPMI-1640 (Hyclone, Logan UT). Consistently, both DMEM and RPMI culture media was supplemented with 10% heat-inactivated fetal bovine serum (FBS: Hyclone), 100 U/ml penicillin and 100 µg/ml streptomycin (Thermo Fisher Scientific Inc., Rockford, IL). The MCF-10A cells were grown in DMEM/F12 supplemented with 10% FBS, 10 µg/ml recombinant human insulin (Sigma), 0.5 µg/ml hydrocortisone (Sigma), 20 ng/ml epidermal growth factor, 2.5 mM L-glutamine, 100 U/ml penicillin, and 100 µg/ml streptomycin. Also, a slight modification of the culture media to the HL-60 and Ovcar 3 cell lines was that 20% of FBS was added to the media (ATCC, Manassas, VA, USA). In addition, Ovcar 3 cells required 10 µg/ml recombinant human insulin (Sigma). The adherent cells, growing in the logarithmic growth phase at a 60-75% confluence, were detached by utilizing a HyQtase enzyme (Thermo Fisher Scientific Inc.), counted and seeded in 96-well plates at 10,000 cells density in 100 µL of culture medium per well. Cells growing in suspension were processed similarly as described above except for the addition of HyQtase. Typically, the incubation conditions of all the cells were at 37° C. in a 5% $CO_2$ humidified atmosphere.

Differential Nuclear Staining Assay to Quantify Cell Death

To analyze the potential cytotoxic activity of PND, the Differential Nuclear Staining (DNS) assay, which was validated for high-throughput screening (HTS) using live-cell bio-imaging was utilized. For this assay, cells were seeded at 10,000 cells/well density in a 96-well plate in 100 µl of culture media, incubated overnight, and treated with a gradient of PND concentrations for 72 h. Two hours before imaging, two fluorescent nucleic acid intercalators were added to each well, Hoechst 33342 and propidium iodide (PI; Invitrogen); at a final concentration of 1 µg/ml each. Due to its high permeability, Hoechst stains all of the cells (total dead and alive), whereas PI only stains dead or dying cells. Montages of 2 by 2 images were captured directly from each individual well of the culture plates by using a multi-well plate reader IN Cell 2000 analyzer, an HTS and high-content analysis (HCA) system (GE Healthcare Life Sciences, Pittsburgh, PA). The following controls were included in every single plate: PBS as solvent/vehicle control, hydrogen peroxide as a positive control for cytotoxicity, and untreated cells to determine the background of toxicity due to cell manipulation and intrinsic factors usually associated with the culture protocol. Each experimental data point, as well as controls, were assessed in triplicates. Cytotoxic concentration 50% (CC50) values were calculated based on a linear interpolation equation. CC50 is defined as the PND concentration required to disrupt the plasma membrane integrity of 50% of the cell population, as compared with solvent-treated cells.

Selective Cytotoxicity Index Calculation

The selective cytotoxicity index (SCI) denotes the capability of a given experimental compound to kill cancer cells more efficiently while inflicting minimal toxicity to non-cancerous origin cells. Thus, the SCI for PND was calculated as follow: SCI=CC50 of non-cancerous cells/CC50 of cancer cells.

Analysis of Phosphatidylserine Externalization Via Annexin V/PI Assay

To determine whether cell death induced by PND was occurring through apoptosis or necrosis, MDA-MB-231 and HL-60 cells were stained with annexin V-FITC and PI and monitored via flow cytometry. Cells were seeded in 24-well plates at a density of 100,000 for adherent MDA-MB-231 and 200,000 HL-60 cells in 1 ml of culture media. After overnight incubation, cells were treated with PND, and incubated for an additional 24 h. For MDA-MB-231 cells, unattached cells were harvested in an ice-cold tube, while adhered cells were detached by using HyQtase (Thermo Fisher) and incubated for around 5 min at 37° C. Both unattached and detached cells harvested from each individual well were washed with ice-cold PBS and centrifuged at 260×g for 5 min. HL-60 were centrifuged directly after the incubation period as they grow in suspension. Cells were then stained with a mixture of annexin V-FITC and PI in 100 µl of binding buffer and incubated on ice in the dark for 15 minutes, following the manufacturer's instructions (Beckman Coulter). Lastly, the cells were resuspended by the addition of 400 µl of ice-cold binding buffer and analysed by flow cytometry (Cytomics FC500; Beckman Coulter). For this series of experiments, cells treated with PBS, as solvent control; treated with $H_2O_2$, as a positive control of cytotoxicity; and untreated were included and processed in parallel. For each sample, 10,000 events/cells were collected and analysed using CXP software (Beckman Coulter). Both the experimental samples and their controls were processed similarly and assessed in triplicate. The sum of both early and late stages of apoptosis was calculated to obtain the total percentage of apoptotic cells.

Polychromatic Analysis of Mitochondrial Membrane Potential

MDA-MB-231 and HL-60 cells were seeded as described in the previous section and treated with PND for 7 h. After treatment, the cells were harvested and stained with 2 µM of the fluorophore 5,5',6,6'-tetrachloro-1,1',3,3'-tetraethylbenzimidazolylcarbocyanine iodide (JC-1) following manufacturer's instructions (MitoProbe; Life Technologies, Grand Island, NY, USA). Cells with healthy polarized mitochondria favour JC-1 to form aggregates, which emit a red signal. Cells that have a depolarized mitochondria exhibit a green signal, due to the dispersed JC-1 monomers. Similar controls as above were concurrently analysed. Data acquisition and analysis were achieved by using CXP software (Beckman Coulter). Each data point was analysed in triplicate.

Analysis of the Transitions Between Cell Cycle Phases

Asynchronous cultures in the exponential growth phase of MDA-MB-231 and HL-60 cells in 24-well plates were treated with several doses of PND. After 72 h of incubation, cells were centrifuged and treated as in the previous section, fixed, permeabilized and stained with a DNA intercalating fluorophore, 4,6-Diamidino-2-phenylindole (DAPI); those three steps were accomplished by adding to the cells 200 µl of a single nuclear isolation medium (NIM)-DAPI solution (Beckman Coulter). The cell suspension was then incubated for an additional 3 min at room temperature in the dark. The controls included in the series of experiments were similar to those described for the above experiments. Approximately, 20,000 events/cells were collected per sample by using a flow cytometer equipped with a solid state 405 nm laser (Gallios; Beckman Coulter). The acquisition and distribution of cell subpopulations within each cell cycle facets were accomplished by utilizing Kaluza flow cytometry software (Beckman Coulter). Additionally, doublets were effectively eliminated by including a single cells gate in the acquisition cell cycle protocol.

DNA Mobility-Shift Assay

Typically, an experimental compound intercalating or binding to double stranded (ds) DNA will increase the molecular mass resulting from forming complexes, decreasing its electrophoretic mobility in an agarose gel, as compared with untreated dsDNA. To explore the potential interaction between PND and dsDNA, a DNA mobility-shift assay was conducted. Each reaction mixture was of 10 µl total volume in PBS pH 7.4. Both PND (Sigma-Aldrich) and quinacrine (Sigma-Aldrich) were tested with three individual concentrations of 1 µM, 0.5 µM or 0.25 µM, respectively. To each reaction mixture, 100 ng of plasmid dsDNA (pCMV-dR8.91; Addgene, Cambridge, MA) was added and the mixture was then incubated for 30 min at 37° C. and stopped by adding 2 µl of 6× gel loading buffer and placed on ice. The potential binding interaction between both PND and quinacrine with dsDNA were analyzed by using 1% (w/v) agarose-gel electrophoresis dissolved in TAE buffer (0.04 M Tris base, 0.04 M acetate and 0.001 M EDTA) pH 8.0. To stain the dsDNA complexes, Ethidium bromide was added to the agarose gel throughout the electrophoresis process at a concentration of 0.5 µg/ml. DNA migration was visualized by utilizing a gel documentation system and pictures were captured by using a UV-light transilluminator (Alpha Innotech, San Leandro, CA). The well-known DNA intercalator fluorescent compound, propidium iodide (PI), was included as positive controls at 1 µg per reaction. As a control, untreated plasmid DNA was included to determine its normal electrophoretic mobility in the gel.

Analysis of the Interaction of PND with Calf Thymus DNA by UV-Visible Spectroscopy UV-Visible measurements were taken in a Varian Cary 100 spectrophotometer. Calf Thymus (CT) DNA and buffers were purchased from Sigma Aldrich. The binding constant of PND with CT DNA was determined by absorption titration at room temperature through stepwise addition of a CT DNA solution (10.1 mM; 5 µL additions) in buffer (5 mM Tris/HCl, 50 mM NaCl, pH=7.39) over a 2 mL working solution of PND (22.8 µM) in the same buffer. Absorption spectra were recorded at 424 nm and the titration was terminated when saturation was reached. In order to determine the binding affinity, the data was fitted to the Scatchard equation r/Cf=K(n−r) (McGhee and von Hippel plots), where r is the number of moles of PND bound to 1 mol of CT DNA, n is the number of equivalent binding sites, and K is the affinity of the complex for those binding sites. Concentrations of free (Cf) and bound (Cb) complexes were calculated from Cf=C(1−α) and Cb=C−Cf, respectively, where C is the total PND concentration. The fraction of the bound complex (α) was calculated from α=(Af−A)/(Af−Ab), where Af and Ab are the absorbances of the free and fully bound drug at the selected wavelengths, and A is the absorbance at any given point during the titration. The plot of r/Cf vs. r gives the binding constant Kb as the slope of the graph [16]. All experiments were performed in triplicate and values of Kb were averaged.

Analysis of the Interaction of PND with Calf Thymus DNA Via Circular Dichroism Spectroscopy Circular dichroism (CD) spectra measurements were taken in a JASCO-1100 spectropolarimeter equipped with a Xenon lamp (JASCO, Easton, MD). CT DNA and buffers were purchased from Sigma Aldrich. A CT DNA stock solution was prepared in Tris/HCl buffer (5 mM Tris/HCl, 50 mM NaCl, pH=7.39) and its concentration (4.325 mM) was spectrophotometrically determined using molar extinction coefficient 6600 M−1 cm−1 at 260 nm. A 150 µM dilution in Tris/HCl buffer was prepared and used for the experiments. A 2.0 mM stock solution of PND was freshly prepared in MQ water prior to use. The appropriate volume of this solution was added to 3 ml working solutions of 150 µM CT DNA to achieve molar ratios of 0.03, 0.06, 0.2 and 0.3 PND/DNA. Samples were prepared in triplicate and incubated for 30 minutes and 20 hours. All CD spectra of DNA and DNA/PND were recorded at 25° C. over the range 205-380 nm and finally corrected with a blank and noise reduction. The final data is the average of three experiments and it is expressed in millidegrees (mdegs).

Statistical Analysis

For each data point, the average of triplicate and their corresponding standard deviations are reported. Statistical significance was determined through two-tailed paired Student's t-tests, and a P value of <0.05 was deemed significant.

Results

PND Exhibits Potent and Selective Cytotoxicity Towards Cancer Cell Lines

The potential cytotoxic effects PND were analysed via a live cell imaging using the differential nuclear staining (DNS) assay, on eleven human cancer cell lines and a non-cancerous control cell line (MCF-10A; FIG. 5). For each individual cell line, dose-response curves were created, also using the DNS assay, to determine the $CC_{50}$ of PND on these cell lines. In general, PND exerted a potent cytotoxicity on all cells tested with consistent $CC_{50}$ values at low micromolar concentrations that ranged from 1.6 µM to 9.4 µM (FIG. 5). As shown in FIG. 6A-B, the effects on various concentrations of PND on the MDA-MB-231 triple negative breast cancer cell line and the HL-60 acute promyelocytic leukemia cell line revealed that PND had $CC_{50}$ values of 1.6 µM and 1.9 µM, respectively (FIG. 6A-B). In these and other assays, untreated cells were used to define the basal levels of dead cells caused by cell manipulation and cell culture. Solvent treated cells were also used as a control for non-specific cell death and for normalization purposes and $H_2O_2$-treated cells were used as a positive control for cytotoxicity (FIG. 6). PND exerted a significant selective cytotoxicity (SCI) index on four out of six of breast cancer cell lines tested, MDA-MB-231, MDA-MB-231 LM2, MDA-MB-468 and MCF-7 with SCI values of 4.13, 2.54, 3.88 and 4.13, respectively, as compared with its non-cancerous breast MCF-10A cells (FIG. 5). Interestingly, the SCI values (<1) were not favourable on T47D and HCC-70 with values below 1 (FIG. 5). In addition, the highest SCI value on the leukemia/lymphoma cells tested corresponded to the HL-60 cell line with an SCI value of 3.5 (FIG. 5). Additionally, PND exhibited an SCI value of 3 and 3.3, for Ramos and Jurkat cells, respectively but poor selectivity was noticed for the CEM cell line (FIG. 5). Good selectivity was detected on the melanoma cell line (SCI=3.2) and two of the three ovarian cancer lines tested (SCI=3.9). However poor selectivity (<2.0) was detected on the pancreatic and lung cancer lines (FIG. 5). Since PND exhibited low $CC_{50}$ values and showed significant selectivity (SCI>3) on both MDA-MB-231 and HL-60 cell lines, they were both selected for further analyses.

PND Elicits Phosphatidylserine Externalization on Both MDA-MB-231 and HL-60 Cells To discern if PND induces its cytotoxicity through apoptosis or necrosis, cells were treated with two different concentrations of PND for 24 h, 34 µM and 68 µM for HL-60 and 11 µM and 22 µM for MDA-MB-231. Subsequently, cells were stained with annexin V-FITC and PI and analyzed via flow cytometry. PND was found to induce significant phosphatidylserine (PS) externalization in both cell lines as compared with positive and negative controls (P<0.001; (FIG. 7A-B). PND induced significant PS externalization in HL-60 cells in a dose-dependent manner, showing 14.8% and 30.2% of apoptotic cells at 34 µM and 68 µM, respectively (P=0.0033, FIG. 7A). Additionally, PND induced a higher percentage of PS externalization in MDA-MB-231 cells than HL-60 cells at both concentration tested with 67.2% and 71.1% annexin positive cells at 11 µM and 22 µM, respectively (FIG. 7B). As expected, solvent treated and untreated cells did not exhibit any significant increment in apoptotic or necrotic death (FIG. 7A-B). Furthermore, H2O2 induced its cytotoxic effect via apoptosis and necrosis on MDA-MB-231 and HL-60 cells, respectively (FIG. 7A-B). Thus PND induced PS externalization in both MDA-MB-231 and HL-60 cells, which is a well-known early event in the activation of apoptosis.

PND Induces Mitochondrial Depolarization on Cancer Cells

An early biochemical event triggering the intrinsic apoptosis pathway is mitochondrial depolarization, which can be quantified by using a polychromatic JC-1 reagent and flow cytometry. JC-1 emits a red or green fluorescence signal when the mitochondria are polarized or depolarized, respectively. Consequently, both MDA-MB-231 and HL-60 cells were incubated for 6 h with PND and the mitochondrial membrane potential (Δψm) status was recorded. As expected based on the PS externalization data, both PND-treated cancer cells revealed significant mitochondrial depolarization, as compared to untreated and solvent treated cells (FIG. 7C-D). These results indicate that PND is able to provoke mitochondrial depolarization in both cancer cell types further indicating that PND induces cell death via the intrinsic apoptosis pathway.

PND Disrupts the Cell Cycle Profile and Displays DNA Fragmentation on MDA-MB-231 and HL-60 Cells To examine how the MDA-MB-231 and HL-60 cells proliferate in the presence of PND, the cell cycle distribution profile was examined via flow cytometry (FIG. 8). To determine the effects of PND on cell cycle progression, a strategy to quantify cellular DNA content that depends on a violet-excited DNA intercalating fluorophore, DAPI (4′,6-diamidino-2-phenylindole) was utilized. After treatment of MDA-MB-231 cells with PND, a significant decrease of the $G_0/G_1$ cell subpopulation was observed; however this effect was not observed in HL-60 cells (FIGS. 8B and F). PND decreased the S and G2/M subpopulations in both MDA-MB-231 and HL-60 cells as compared with PBS and untreated controls (FIGS. 8B-D and F-H). Additionally, PND caused significant DNA fragmentation in a concentration-dependent fashion in both cancer cell lines, as denoted by a significant increase in the sub-G0/G1 subpopulation ($P<0.0005$; FIGS. 8A and E). Differences in the percentages of both cells in each phase of cell cycle between PBS-treated and untreated cells were essentially indiscernible. These experiments revealed that PND disrupted the distribution of the cell cycle profile and induced DNA fragmentation (sub-G0/G1 population) in both cancer cell types.

PND Interacts Directly with dsDNA

The potential interaction between PND and dsDNA was examined with the use of a DNA mobility-shift assay using plasmid DNA as a binding substrate, and compared to that of quinacrine, a compound with comparable structure, and a well-known DNA intercalator. When 1 mM of PND was incubated with DNA a marked reduction of migration of PND-treated DNA was observed, as compared with free plasmid DNA (shifts are indicated to the left side of FIG. 9). Approximately half of the total input DNA was located at the loading well with minimum mobility into the agarose gel. Furthermore, when 0.5 and 0.25 mM of PND were incubated with DNA, there was a clear reduction in mobility (noted to the left side of FIG. 9). Additionally, PND-treatment did not result in DNA degradation based on the absence of DNA fragments smaller than the free supercoiled DNA (FIG. 9). In previous studies, quinacrine, with a similar chemical structure to PND, was also found to interact with DNA by intercalation. As shown in FIG. 9, quinacrine caused the maximum retardation of DNA mobility at the highest concentration tested (1 mM) as evidenced by a smear, indicative of complexes with supercoiled DNA. Also, quinacrine provoked a clear retardation mobility of the DNA, similar to PND, when tested at 0.5 and 0.25 mM (FIG. 9). As was the case with DNA treated with PND, quinacrine did not exhibit any DNA degradation activity (FIG. 9). PI, which was used a positive control for DNA binding, also provoked retardation of the DNA mobility. Our results clearly indicate that PND can interact directly with DNA provoking its mobility-shift in agarose gels, and the similar behaviour to that of quinacrine might suggest that PND has also the ability to intercalate between the bases of dsDNA.

PND Intercalates with DNA as Determined by UV-Visible Spectrophotometric Titration In order to further prove the intercalative interaction of PND with CT DNA, spectrophotometric titrations were performed in Tris/HCl buffer. PND displays strong absorption bands in the region 300-500 nm typical for transitions between electron energy levels of conjugated aromatic rings. In general, hypochromic and batochromic effects observed on maxima of UV-Visible absorbance can be taken as evidence of stacking interactions between conjugated aromatic systems that intercalate the nucleobases of DNA. FIG. 10A shows the absorption spectra of PND in the studied region upon consecutive additions of CT DNA. The maximum of absorbance at 424 nm was studied to diagnose the compound-DNA interaction. Our results show a significant hypochromic effect (39%) and a red-shift of 8 nm. In addition, the Scatchard equation was used to determine the binding affinity [8.5±0.7×105 M−1] of PND to CT DNA. All binding data of PND with CT DNA, shown in FIG. 10B, are comparable to that of well-known intercalating agents with similar structure, and indicate that PND is also able to intercalate between the bases of DNA, as suggested by the mobility-shift assay.

PND Stabilizes the B Conformation of CT DNA as Observed by Circular Dichroism Spectroscopy In addition, detailed DNA conformational alterations were studied by means of circular dichroism spectroscopy in Tris/HCl buffer. A typical CD spectrum of CT DNA in its B form shows a positive band with a maximum at 275 nm due to base stacking, and a negative band with a minimum at 248 nm due to right-handed helicity. Therefore, changes in the CD signals can be assigned to corresponding changes in DNA secondary structure. FIGS. 11, A and B shows the CD spectrum of CT DNA, and the effect of treating it with increasing amounts of PND for 30 minutes and 20 hours, respectively. Our results show that PND was able to increase the intensity of both the negative and the positive bands in a concentration-dependent manner but with no significant red-shifts in any of them. These results are comparable to previously reported similar compounds, and suggest that PND is able to stabilize the right-handed B form of DNA with no significant conformational changes. The fact that the same spectral changes were observed upon 30 minutes and 20 hours incubations suggests that the kind of interaction taking place occurs in a few minutes, confirming the intercalative mode of binding. In addition, a positive signal appeared in the range 300-340 nm, a region where DNA does not absorb light, suggesting that some asymmetrical change is possibly being induced on PND upon binding to CT DNA, since no signal for PND is observed in the absence of the nucleic acid (see FIG. 10, C).

Discussion

In all the cancer cell lines analyzed, PND treatment was found to cause cell death at low micromolar concentrations (from 1.6 µM to 9.4 µM). Apart from being less toxic for non-cancerous cells (MCF-10A; CC50 of 6.6 µM), PND displayed favourable selectivity on several breast cancer cells, as compared with non-cancerous cells, with an SCI value >2.5. PND also exhibited favourable SCI values (from 1.43 to 3.47) on leukemia/lymphoma cells showing the highest selectivity on HL-60 cancer cells.

The mode of action of PND was analyzed in both the MDA-MB-231 and HL-60 cancer cell lines. After exposure to a toxic agent, cells can undergo two main routes, necrosis or apoptosis pathways. Phosphatidylserine (PS) is preferentially located on the inner side of the plasma membrane leaflet, facing the cytosol, and when cells initiate the apoptosis pathway, it is translocated to the outer leaflet of the plasma membrane, which is a biochemical hallmark of apoptosis. Flow cytometry identified this apoptotic facet when using propidium iodide and FITC-conjugated annexin V which has high affinity for PS. PND-treated MDA-MB-231 and HL-60 cells consistently exhibited PS externalization, suggesting that PND uses the apoptosis pathway to inflict its cytotoxicity in a dose-dependent manner.

Furthermore, apoptosis can be initiated via intrinsic or extrinsic biochemical pathways. A critical biochemical event triggering the activation of the intrinsic pathway is through mitochondrial depolarization. Therefore, MDA-MB-231 and HL-60 cells were exposed to PND and stained with the polychromatic JC-1 reagent, to investigate whether the mitochondrial depolarization was involved in its mechanism to induce cell death. Our data clearly indicate that both cancer cell lines exhibited a significant mitochondrial depolarization after exposure to PND, indicating that the intrinsic apoptosis pathway is involved in its cytotoxic mechanism.

A well-established strategy to study the cell cycle profile relies on quantifying the cellular DNA content via flow cytometry. When using this approach, it is possible to distinguish three phases of the cell cycle, the G0/G1, S, and G2/M. In addition, independently of which initiation signal is used to activate the apoptotic cascade, the death signal ultimately results in DNA fragmentation; a late biochemical hallmark of apoptosis. When performing the cell cycle analysis via flow cytometry, cells undergoing DNA fragmentation are easy to identify by the presence of a sub-G0/G1 subpopulation, a distinct peak localized to the left side of the cell cycle histograms. Thus, the occurrence of apoptosis-induced DNA fragmentation as well as the cell cycle was analyzed concomitantly, after incubating the cells with PND for 72 h. These assays revealed that PND was able to disturb the progression of the cell cycle profile on MDA-MB-231 and HL-60 cells, detecting a dissimilar pattern from each cell line. In addition, PND caused consistent DNA fragmentation on both MDA-MB-231 and HL-60 cells in a dose-dependent fashion, confirming the previous results that PND induces apoptosis.

The interaction between DNA and drugs or proteins can be readily detected by the retardation of DNA migration during the mobility-shift assay via gel electrophoresis. In these DNA binding assays, the experimental compound-DNA complexes migrate more slowly than the free DNA (uncomplexed DNA control), which results in DNA having a heavier molecular weight. Additionally, when incubating a chemical compound with plasmid DNA, it is possible to detect if there are any deleterious effects resulting in DNA degradation or fragmentation. The results indicate that PND interacts directly with DNA since it causes significant DNA retardation in agarose gels, in a concentration-depended manner but did not cause DNA degradation. The intercalative mode of DNA binding of PND was confirmed by UV-Visible spectrophotometric titrations as well as circular dichroism of CT DNA. In addition, CD spectra provided evidence of CT DNA stabilization in its B form with no detectable conformational changes upon interaction with PND. Collectively, the mobility-shift assay, UV-Visible and CD series of experiments, provide compelling evidence that PDN binds DNA by intercalating with nucleobases of the DNA.

In this preclinical study, the findings indicate that PND displays potent cytotoxicity, with low micromolar CC50 values and favourable selective cytotoxicity index, towards a panel of human cancer cells, showing significant selectivity against triple negative breast cancer MDA-MB-231 cells (a class of aggressive tumours) and leukemia HL-60 cells. PND and related compounds and derivatives have activity as anti-cancer drugs, since PND markedly and consistently inflicts its cytotoxic effect by activating the apoptosis pathway, as evidenced by PS externalization, mitochondrial depolarization, DNA fragmentation, and interfering with the cell cycle. Furthermore, PND was found to interact directly with DNA by causing a DNA retardation during agarose gel electrophoresis, and spectral changes in the UV-Visible profile of PND, as well as the CD spectra of DNA, suggesting an intercalative binding mode.

Example 4

Analysis of PND Activity on Metastatic Breast Cancer in Mice

Material and Methods 12 comparable mice with metastatic breast cancer cells from the cell line MDA-MB-231 LM2-LUC4 were injected with either aqueous solution of pyronaridine (PND) or placebo (water), every day using the gavage force-feeding technique. Treatment began when tumors reached 150-300 mm$^3$ in size (i.e. Day 1).

In the PND-treated group (n=6), all 6 mice were given 160 mg/kg from Day 1 to Day 9. PND-treated mice numbers 2, 4, and 5 received 160 mg/kg for the entire study, while PND-treated mice numbers 1, 3, and 6 had the largest tumors in the group on Day 9, and had their doses increased on Day 10 to 240 mg/kg, and again on Day 13 to 320 mg/kg. The control mice (n=6) were given placebo throughout the study. The size of each tumor was measured daily. The protocol's endpoint was when a tumor reached 1500 mm$^3$ in size, triggering the euthanization of the mouse. For the analysis, the level of significance was set at $P<0.05$.

Results

A comparison of tumor sizes from Day 1 to 9 showed that on average the tumors had grown larger in the control mice (750 mm$^3$) than in the PND-treated mice (430 mm$^3$). The difference was significant, t-test P-value of 0.01 (see FIG. 12A). A comparison of the tumor sizes from Day 1 to 15 (when all 12 mice were alive) showed that, on average, the tumors had grown larger in the placebo group than in the PND-treated group, and the difference was significant, t-test P-value of 0.0001 (see FIG. 12B).

There was a significant difference in lengths of survival favoring the PND-treated group, though, following Day 15, comparisons became more complicated due to the increased doses in 3 PND-treated mice and due to the euthanization of placebo mice.

During the study, there were no reports of negative adverse events except discomfort in walking after Day 15. All 6 PND-treated mice at about Day 20 showed a yellowing in the eyes, skin, ears, and paws likely due to the fact that PND is a strong yellow pigment. There was no weight loss, no eating disorders, or grooming issues observed. The 6 PND-treated mice were dissected and there was no sign of PND accumulation anywhere including in the stomach, intestines, or liver.

The results clearly demonstrated that in the PND-treated mice, metastatic breast cancer tumors grow smaller and the mice live longer than in mice given placebo.

Example 5

Analysis of PND Activity in Conjunction with Chemotherapy

Material and Methods

PND was added to cultures of the MDA-MB-231 breast cancer line 24 hours after the cells were treated with a selection of known commercial chemotherapeutic drugs, before the cells were analyzed for cell death. Each of the drugs are known to have serious side-effects at the does commonly administered for the treatment of cancer. The dose of the chemotherapeutic drugs was reduced to one half, one fourth, one eighth, and one sixteenth of the initial dose; while the dose of PND was kept the same. The effect of these combinational therapies was measured by the concentration of each compound needed to be cytotoxic to at least 50 percent of cancer cells (CC50). For cisplatin, gemcitabin, bortezomib and MG132, the initial dose (CC50) was 95.42 $\mu$M, 0.44 $\mu$M, 0.01 $\mu$M, and 0.5 $\mu$M, respectively, while the dose of PND was kept constant at 5.5 $\mu$M.

Results

The results shown in FIG. 12 demonstrate that the co-administration of PND (wherein the PND is administered after the chemotherapeutic drug) can greatly reduce the amount of drug required to effectively kill the cancer cells.

Example 6

Treatment of Late Stage Cancer in Canines with PND

Materials and Methods

An open-label study was conducted to assess the efficacy in increasing longevity and to assess the safety of oral pyronaridine tetraphosphate (PND) in five terminally-ill canine cancer patients.

Eligible patients had a malignancy that was metastatic or unresectable and for which standard curative or palliative measures did not exist or were no longer effective. Due to ethical concerns of treating terminally-ill dogs, there was no placebo group.

The PND was obtained from Mangalam Drugs and Organics, Ltd., and was encapsulated in gelatin capsules for orally administration twice a day.

The primary outcome assessed was the difference between the patient's expected survival length estimated at the time of study entry and his or her actual survival length.

The secondary outcomes were: anti-tumor activity, malignancy-associated symptom relief, and the safety and tolerability of PND.

The study on the five canines was as follows:

Case 1, Mast cell carcinoma: Dog (Golden Retriever), female, 6 years old, 28.7 kg. Cancer was confirmed by histopathology report. In mid-May 2019 the administration of oral PND to the dog began after which patient received no other cancer medication. Veterinarian expected survival length of between 4 and 6 months at the time of study entry. Patient received 23 mg/kg/day PND (325 mg in the morning and 325 mg in the evening).

Case 2, Osteosarcoma: Dog (Saint Bernard), male, 5 years old, 49.7 kg. On 17 May 2019 the administration of oral PND began after which the patient received no other cancer medication. The veterinarian expected a survival length of between 4 and 6 months at the time of study entry. Patient received 20 mg/kg/day PND (325 mg in the morning and 650 mg in the evening).

Case 3, spindle cell sarcoma: Dog (Border Collie), male, 9 years old, 28.5 kg. In 2014 the dog was diagnosed with a low-grade spindle cell sarcoma, and was due to be euthanized on 11 Feb. 2019, with a life expectancy of 1-2 weeks. Instead, the veterinarian began the administration of oral PND on 11 Feb. 2019 after which patient received no other cancer medication. Patient received 15 mg/kg/day PND (215 mg in the morning and 215 mg in the evening).

Case 4, non-Hodgkin lymphoma: Dog (Boxer), female, 27 kg, 11 years old. Cancer was confirmed by biopsy report. In December 2018 the administration of oral PND to the dog began after which patient received no other cancer medication. Patient received 15 mg/kg/day PND (210 mg in the morning and 210 mg in the evening). However, the administration of PND stopped in February 2019 (due to shipping problems from the USA to Canada) and never resumed.

Case 5, mast cell tumor: Dog, male, 27.9 kg. Cancer was confirmed by histopathology report. A tumor was surgically excised from tongue, and there was no clean border. In December 2018 the administration of oral PND began after which the patient received no other cancer medication. Patient received 15 mg/kg/day PND (210 mg in the morning and 210 mg in the evening).

Results

Case 1: There were no reports of any study-drug related adverse events. The volumes of four tumors were measured at time of study entry and compared with follow-up measurement. Right mandibular node 2.5 cm×2 cm versus 2 cm×1 cm; Left mandibular node 3 cm×2 cm versus 2.2 cm×1 cm; Right popliteal (back of knee) node 0.5 cm×0.5 cm versus 0.2 cm×0.2 cm; and Left popliteal node: 0.5 cm×0.5 cm versus 0.2 cm×0.2 cm. The dog was still alive, and the malignancy-associated symptom relief permitted daily activities as of June 2019. In all cases at follow-up measurement the tumor volume had been reduced in size by a clinically significant amount.

Case 2: The only reports of possible study-drug related adverse events were drooling, facial swelling, and vomiting which was resolved with diphenhydramine. Tumor size at time of study entry was 3.7 cm×2.6 cm. As at June 2019, the dog was still alive and in good shape as the malignancy-associated symptom relief permitted daily activities.

Case 3: There were no reports of any study-drug related adverse events except initial vomiting, which was controlled. The volumes of three tumors were measured at the time of study entry: 2 cm×2.5 cm; 3 cm×3.8 cm; and 3 cm×4 cm. On follow-up the volume of each tumor was reported to have been reduced by approximately 20%. In mid-May 2019 the dog was euthanized, the dog's survival was lengthened by 3 months.

Case 4: There were no reports of any study-drug related adverse events. The volume of one tumor on the patient's neck was measured at time of study entry and compared with follow-up measurement. The tumor had shrunk by 70% by March 2019. On 20 Apr. 2019 the dog was euthanized, the dog's survival was lengthened by 2.5 months.

Case 5: Patient had an enlarged left mandibular. The volume of one tumor was measured at time of study entry and compared with follow-up measurement. The tumor remained the same volume: 2 cm×1 cm versus 2 cm×1 cm. The dog was still alive, and the malignancy-associated symptom relief permitted daily activities as of June 2019.

Example 6

Treatment of Late Stage Cancer in Humans with PND

Materials and Methods

An open-label, dose-escalating study was conducted to assess the longevity and safety of oral pyronaridine tetraphosphate (PND) in five terminally-ill human patients with selected cancers. Eligible patients had a malignancy that was metastatic or unresectable and for which standard curative or palliative measures did not exist or were no longer effective. Exclusion criteria included active clinically significant infection, uncontrolled intercurrent illness, neutropenia, and pregnancy.

The PND was obtained from Mangalam Drugs and Organics, Ltd, and the powered PND was encapsulated in size "00" gelatin capsules for oral administration. Each capsule contained either 125 mg of PND and the inert filler microcrystalline cellulose (MCC) or 200 mg PND (no filler).

Prior to study entry and prior to each dose escalation, that the patient's complete blood count (CBC) and comprehensive metabolic panel (CMP) laboratory results were within normal reference ranges was verified.

Patient were instructed to escalate his or her dose if there was no unacceptable toxicity. Study Arm 1 started with a daily dose of 250 mg for 2 weeks, then 375 mg for 2 weeks, then 500 mg onwards. Study Arm 2 started with a daily dose of 200 mg for 2 weeks, then 400 mg for 2 weeks, then 600 mg onwards. Due to ethical concerns of treating terminally-ill patients, there was no placebo group.

The primary outcomes assessed was the difference between the patient's expected survival length estimated at the time of study entry (estimated at 2-4 weeks for each patient) and his or her actual survival length. The secondary outcomes were malignancy-associated symptom relief, anti-tumor activity, safety, and tolerability of PND.

The study on the five humans was as follows:

Case 1, Male, age 65, Hepatic bile duct Klatskin (or hilar cholangiocarcinoma) diagnosed in March 2018. On 20 Dec. 2018, patient started taking PND as per protocol, 2 capsules/day.

Case 2, Male, age 43, Lung cancer, stage IV, diagnosed in May 2017. Patient was administered chemotherapy with the last cycle in December 2018, and on 22 Jan. 2019, started taking PND 2 capsules/day.

Case 3, Female, age 55, Ovarian cancer, stage IV, diagnosed in June 2017. Patient was administered chemotherapy with the last cycle in November 2018, and on 15 Jan. 2019, started taking PND 2 capsules/day.

Case 4, Female, age 54, Breast cancer, stage IV, diagnosed in September 2017. On 20 Jan. 2019, patient started taking PND 2 capsules/day.

Case 5, Female, age 40, Small cell lung cancer, stage IV, diagnosed in April 2017. Patient was administered chemotherapy with the last cycle in December 2018, and on 29 Jan. 2019, started taking PND 2 capsules/day.

Results

Case 1: There were no reports of any study-drug related adverse events. In June 2019, the patient was still alive, his most recent CBC and CMP results were within normal reference ranges, and his malignancy-associated symptom relief permitted daily activities.

Case 2: There were no reports of study-drug related adverse events. The patient passed away on 22 Feb. 2019 from lung cancer.

Case 3: There were no reports of study-drug related adverse events. The patient passed away on 29 Jan. 2019 from ovarian cancer.

Case 4: Patient passed away on 15 Feb. 2019 from breast cancer.

Case 5: The only report of a study-drug related adverse event was irritation on the skin during the first week of treatment which cleared within a week, possibly study-drug related. As at June 2019, patient was still alive, her most recent CBC and CMP results were within normal reference ranges, and her malignancy-associated symptom relief permitted daily activities.

PND appears to be well tolerated (the maximum tolerated dose was not reached for any patient) and at to have extended the lives of 2 in 5 cancer patients, there is justification for adequate and well-controlled studies leading to an approved PND-based cancer drug that increases survival rates without serious side effects.

The invention claimed is:

1. A method of selectively inducing apoptosis in proliferating cancer cells for the treatment of cancer in a subject, the method comprising the step of administering to the subject a composition comprising a therapeutically effective amount of pyronaridine (PND), or a pharmaceutically acceptable salt thereof, once, twice, three, four or five times daily or every second or third day, or once every week, or once every two weeks, wherein the therapeutically effective amount of PND, or pharmaceutically acceptable salt thereof, is at least about 100 mg, and the PND, or pharmaceutically acceptable salt thereof, induces said apoptosis, wherein the method does not include administration of another chemotherapeutic agent and wherein the administration has selective toxicity to actively dividing cancer cells.

2. The method of claim 1, wherein the cancer is a tumour that is a carcinoma selected from the group consisting of pancreas, bladder, breast, colon, mesothelioma, kidney, liver, lung, including small cell lung cancer, non-small cell lung cancer, head and neck, oesophagus, gall bladder, ovary, stomach, cervix, thyroid, prostate and skin cancer, or a tumour that is a sarcoma selected from the group consisting of fibrosarcoma, rhabdomyosarcoma, chondrosarcoma, leiomyosarcoma, mesothelial sarcoma, angiosarcoma, liposarcoma, or a tumour of the central and peripheral nervous system selected from the group consisting of astrocytoma, neuroblastoma, glioma and schwannomas, or other tumours selected from the group consisting of melanoma, seminoma, teratocarcinoma, osteosarcoma, xenoderoma pigmentosum, keratoctanthoma, thyroid follicular cancer and Kaposi's sarcoma, or a liquid (blood cancer) selected from the group consisting of B-cell lymphoma, T-cell lymphoma, Hodgkins lymphoma, non-Hodgkins lymphoma, hairy cell lymphoma, mantle cell lymphoma, myeloma, Burkett's lymphoma, extranodal lymphomas of the stomach, breast or brain, plasma cell myeloma, Kahler's disease, multiple myeloma, myelogenous leukemia, granulocytic leukemia, lymphatic leukemia, lymphocytic leukemia, and lymphoblastic leukemia.

3. The method claim 2, wherein the cancer is a breast cancer.

4. The method of claim 2, wherein the cancer is a lymphoma.

5. The method of claim 1, wherein the therapeutically effective amount of PND, or pharmaceutically acceptable salt thereof, is about 100 mg to about 1000 mg.

6. The method of claim 5, wherein the PND, or pharmaceutically acceptable salt thereof, is administered every second day.

7. The method of claim 1, wherein the PND or pharmaceutically acceptable salt thereof, is administered once daily.

8. The method of claim 2, wherein the cancer is a tumour and the PND, or pharmaceutically acceptable salt thereof, induces apoptosis in proliferating cancer cells in the tumour, thereby reducing the size of the tumour.

9. A method of selectively inducing apoptosis in proliferating cancer cells for the treatment of cancer in a subject, the method consisting of the step of administering to the subject a composition consisting of a therapeutically effective amount of pyronaridine (PND), or a pharmaceutically acceptable salt thereof, and an excipient, once, twice, three, four or five times daily or every second or third day, or once every week, or once every two weeks, wherein the therapeutically effective amount of PND, or pharmaceutically acceptable salt thereof, is at least about 100 mg, and the PND, or pharmaceutically acceptable salt thereof, induces said apoptosis, wherein the administration has selective toxicity to actively dividing cancer cells.

* * * * *